US008993800B2

(12) United States Patent  
Ohishi et al.

(10) Patent No.: US 8,993,800 B2
(45) Date of Patent: Mar. 31, 2015

(54) PROCESS FOR PRODUCING OPTICALLY ACTIVE α-METHYLCYSTEINE DERIVATIVE

(71) Applicant: Kaneka Corporation, Osaka (JP)

(72) Inventors: Takahiro Ohishi, Takasago (JP); Hirokazu Nanba, Takasago (JP); Masanobu Sugawara, Takasago (JP); Masashi Izumida, Takasago (JP); Tatsuya Honda, Takasago (JP); Kohei Mori, Takasago (JP); Satohiro Yanagisawa, Takasago (JP); Nobuo Nagashima, Takasago (JP); Kenji Inoue, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 13/897,079

(22) Filed: May 17, 2013

(65) Prior Publication Data

US 2013/0261331 A1     Oct. 3, 2013

Related U.S. Application Data

(62) Division of application No. 12/757,947, filed on Apr. 9, 2010, which is a division of application No. 10/515,658, filed as application No. PCT/JP03/07108 on Jun. 5, 2003, now abandoned.

(30) Foreign Application Priority Data

Jun. 5, 2002  (JP) ................. 2002-164598  
Aug. 16, 2002  (JP) ................. 2002-237698  
Mar. 12, 2003  (JP) ................. 2003-067299

(51) Int. Cl.
| | |
|---|---|
| C07C 315/00 | (2006.01) |
| C12P 13/12 | (2006.01) |
| C07C 319/06 | (2006.01) |
| C07D 233/76 | (2006.01) |
| C12P 17/04 | (2006.01) |
| C12P 17/10 | (2006.01) |
| C12P 41/00 | (2006.01) |

(52) U.S. Cl.
CPC .............. *C12P 13/12* (2013.01); *C07C 319/06* (2013.01); *C07D 233/76* (2013.01); *C12P 17/04* (2013.01); *C12P 17/10* (2013.01); *C12P 41/009* (2013.01)
USPC .......................... 562/556; 548/319.1; 435/189

(58) Field of Classification Search
CPC ...... C07C 323/58; A61K 38/4886; C12N 9/00
USPC .......................... 562/556; 548/319.1; 435/189
See application file for complete search history.

(56) References Cited

U.S. PATENT DOCUMENTS

| | | | |
|---|---|---|---|
| 4,812,406 | A | 3/1989 | Takahashi et al. |
| 5,338,859 | A | 8/1994 | Bhattacharya |
| 5,707,837 | A | 1/1998 | Drauz et al. |
| 6,407,281 | B1 | 6/2002 | Ueda et al. |
| 6,914,158 | B2 | 7/2005 | Webber et al. |

FOREIGN PATENT DOCUMENTS

| | | |
|---|---|---|
| EP | 175312 A2 | 3/1986 |
| EP | 725142 A1 | 8/1996 |
| EP | 801131 A1 | 10/1997 |
| JP | 49-48534 B1 | 12/1974 |
| JP | 50-106901 A | 8/1975 |
| JP | 56-58493 A | 5/1981 |
| JP | 61-072762 A | 4/1986 |
| JP | 62-056457 A | 3/1987 |
| JP | 03-095145 A | 4/1991 |
| JP | 07-222593 A | 8/1995 |
| JP | 2001-120295 A | 5/2001 |
| WO | 00/40545 A1 | 7/2000 |
| WO | 01/72702 A2 | 10/2001 |
| WO | 02/074750 A1 | 9/2002 |

OTHER PUBLICATIONS

Nagarajan et al, Indian Journal of Chemistry, Section B: Organic Chemistry Including Medicinal Chemistry (1981), 20B(8), 672-9.*
Ohishi et al, Tetrahedron Letters, 2007, 48, 3437-3440.*
Fujii et al, Chem.Phar.Bull. 1987, 35, 3447.*
Almstead et al, Phosphorus, Sulfur and Silicon, 1999, vol. 144-146, pp. 325-328.*
Tahara et al, "Studies on alpha-alkyl-alpha amino acids. Part I. Synthesis on S-alkyl-2-methyl-DL-cysteines," Agricultural and Biological Chemistry, Japan Soc. for Bioscience, Biotechnology and Agrochem, Tokyo, Japan, vol. 35, No. 1, Jan. 1, 1971, pp. 53-57; XP 002973997.
Oh et al. Bulletin of the Korean Chemical Society, 1988 9(4), pp. 231-235.
Herbert T. Nagasawa et al., β-Substituted Cysteines as Sequestering Agents for Ethanol-Derived Acetaldehyde in Vivo; J. Med. Chem., vol. 30, pp. 1373-1378, 1987.
Holger Lickefett et al., Enantioseparation of 5-Monosubstituted Hydantoins by Capillary Gas Chromatography- Investigation of Chemical and Enzymatic Racemization; Tetrahedron Asymmetry, vol. 4, No. 6, pp. 1129-1135, 1993.
Nicholas A. Meanwell et al., 1,3-Dihydro-2H-imidazo[4,5-b] quinolin-2-ones-Inhibitors of Blood Platelet cAMP Phosphodiesterase and Induced Aggregation; J. Med. Chem., vol. 34, pp. 2906-2916, 1987.
Mulqueen et al., "Synthesis of the Thiazoline-based Siderophore(S)-Desferrithiccin" Tetrahedron, vol. 49, No. 24, pp. 5359-5364, 1993.
Pattenden et al., "Enantioselective Synthesis of 2-Alkyl Substituted Cysteines" Tetrahedron vol. 49, No. 10, pp. 2131-2138, 1993.
Nyc et al., "Synthesis of Orotic Acid from Aspartic Acid" J. Am. Chem. Soc., 1947, vol. 69, p. 1382-4.

* cited by examiner

*Primary Examiner* — Sudhakar Katakam
(74) *Attorney, Agent, or Firm* — Sughrue Mion, PLLC

(57) ABSTRACT

The present invention provides a simple industrial process for producing an L- or D-optically active α-methylcysteine derivative or its salt, which is a useful pharmaceutical intermediate, from readily available, inexpensive raw materials. In a process for producing an L- or D-optically active α-methylcysteine derivative or its salt, a racemic N-carbamoyl-α-methylcysteine derivative or its salt is D-selectively cyclized with hydantoinase to produce a D-5-methyl-5-thiomethylhydantoin derivative or its salt and an N-carbamoyl-α-methyl-L-cysteine derivative or its salt, which are then subjected to deprotection of the amino group and the sulfur atom, and hydrolysis.

12 Claims, No Drawings

PROCESS FOR PRODUCING OPTICALLY ACTIVE α-METHYLCYSTEINE DERIVATIVE

This application is a divisional of Ser. No. 12/757,947 filed Apr. 9, 2010, which is a divisional of Ser. No. 10/515,658, filed Jan. 6, 2006 (now abandoned), which is a national stage of International Application No. PCT/JP03/07108 filed on Jun. 5, 2003 claiming priority to Japanese Application No. 2002-164598 filed on Jun. 5, 2002, No. 2002-237698 filed on Aug. 16, 2002, and No. 2003-67299 filed on Mar. 12, 2003, all of which are incorporated herein by reference in their entireties.

TECHNICAL FIELD

The present invention relates to a process for producing an optically active L- or D-α-methylcysteine derivative or its salt which is useful as an intermediate for pharmaceutical products.

BACKGROUND ART

Known processes for producing an optically active L- or D-α-methylcysteine derivative or its salt include the following:

1) A process asymmetric methylation of an optically active thiazolidine compound produced from optically active cysteine and pivalaldehyde (WO01/72702).

2) A process of asymmetric thiomethylation of an optically active oxazolone compound produced from optically active alanine and benzaldehyde (J. Org. Chem., 1996, 61, 3350-3357).

3) A process of methylation of a thiazoline compound produced from cysteine and cyanobenzene, and isolating and purifying the resulting racemic thiazoline compound by chiral HPLC (Synlett., 1994, 9, 702-704).

4) A process of asymmetric bromomethylation of an optically active diketopiperazine compound synthesized from optically active valine and alanine, and replacement of the bromine atom of the resulting compound by an alkali metal alkylthiolate (Synthesis, 1983, 37-38).

5) A process for the reaction of thiol with the optically active aziridine which is prepared from the optically active 2-methylglycidol obtained by Sharpless asymmetric oxidation of 2-methyl-2-propene-1-ol (J. Org. Chem., 1995, 60, 790-791).

6) A process of methylation of aminomalonic acid derivatives, desymmetrization of the product with pig liver esterase (abbreviated as "PLE" hereinafter), and reaction of the resulting asymmetric ester with an alkali metal thioacetate (J. Am. Chem. Soc., 1993, 115, 8449-8450).

Any of processes 1) to 4) requires low-temperature reaction with an expensive base such as butyl lithium. Process 5) is complicated by a large number of steps, and requires various kinds of expensive reagents. The key step of process 6) is the desymmetrization of the diester by PLE as esterase etc., but PLE cannot be easily stably secured on an industrial scale because of difficulty in mass production of PLE, thereby making the process unpractical. Therefore, any one of the processes has problems to be solved as an industrial process for producing an optically active methylcysteine derivative or its salt.

The optically active methylcysteine derivative produced by any one of the above-described processes and the like(,) can be converted to optically active α-methylcysteine or its salt by appropriate deprotection if necessary. The resulting optically active α-methylcysteine or its salt is preferably isolated and purified by crystallization. However, there has been no known example of isolation of optically active α-methylcysteine or its salt by crystallization. Only the above-described WO01/72702 etc. disclose examples of isolation. These examples relate to a method in which a thiazolidine compound which is an optically active α-methylcysteine derivative is deprotected with hydrochloric acid, resulting an aqueous solution of optically active α-methylcysteine or its salt is concentrated to produce a solid, and in some cases, the solid is washed with an organic solvent to isolate the compound. However, as a result of isolation of the compound according to this method, the inventors have found that a solid is precipitated with concentration of the aqueous solution, and at the same time, the solid becomes a large lump containing water to make stirring difficult. Also, when concentration is continued, the solid strongly adheres to the wall and comes to a non-fluid state. Therefore, the operation of concentrating the aqueous solution to precipitate a solid is disadvantageous as an industrial operation, and the solid tends to be aggregated with concentration. This causes difficulty in stirring a crystallization solution and isolating the solid. Therefore, the isolation methods disclosed in the above WO01/72702 etc. are unsuitable for industrial production.

Furthermore, if the insoluble inorganic salts generate and are mixed in the optically active α-methylcysteine or its salt obtained by deprotection of optically active methylcysteine derivative during the reaction or a post-treatment step like neutrization etc., the inorganic salt cannot be removed by the above-described conventional method.

Furthermore, α-methylcysteine or its salt is unstable against oxidation and is easily converted to a disulfide by dimerization. For example, dimerization of cysteine having a similar structure rapidly proceeds to produce cystine (Protein Chemistry 1, Amino Acid Peptide, Kyoritsu Shuppan, p. 326). Also, dimerization of α-methylcysteine proceeds to produce a disulfide, and the disulfide cannot be easily removed and is unavoidably mixed in a product. Therefore, it is important to establish a process capable of significantly suppressing the production and mixing of a disulfide.

It is thus strongly demanded to establish an industrially practical process for appropriately crystallizing a high-quality optically active α-methylcysteine or its salt to obtain the compound as crystals.

Apart from the conventional processes, a conceivable process for simply producing an optically active α-methylcysteine derivative is to convert a racemic α-methylcysteine derivative to an optically active α-methylcysteine derivative by enzymatic resolution. In order to realize this method, it is important to establish a process for producing a racemic α-methylcysteine derivative to be supplied to optical resolution and enzymatic reaction having high optical resolution ability. It is also important to properly select a racemic α-methylcysteine derivative to be supplied to the enzymatic optical resolution.

In order to realize the process using enzymatic optical resolution, it is required that a racemic α-methylcysteine derivative used as a substrate can be simply effectively produced, conforms to the substrate specificity of an enzyme, and has a protecting group or an auxiliary group suitable for achieving high stereoselectivity, and the protecting group or auxiliary group can be simply removed after enzymatic reaction. From this viewpoint, a preferred racemic α-methylcysteine derivative is an N-carbamoyl-α-methylcysteine derivative.

It has been known for a long time that hydantoinase known as a hydrolase for ring opening of hydantoin also catalyzes a reverse reaction of converting N-carbamoyl-α-amino acid to corresponding 5-substituted hydantoin. It is thus expected that one of the optical isomers of the racemic N-carbamoyl-α-methylcysteine derivative is selectively converted to hydantoin with the enzyme and subjected to optical resolution. The optically active N-carbamoyl-α-methylcysteine derivative obtained by optical resolution can easily be converted to an optically active α-methylcysteine derivative by decarbamoylation. The other product of the optical resolution, i.e., an optically active 5-methyl-5-thiomethylhydantoin derivative, is equivalent to an optically active α-methylcysteine derivative and can thus be led to an optically active α-methylcysteine derivative (having a configuration reverse to that of the product directly obtained by optical resolution) through ring-opening hydrolysis and decarbamoylation.

The racemic N-carbamoyl-α-methylcysteine derivative can be produced by combination of a general chemical method for synthesizing an amino acid and N-carbamoylation reaction. However, a process for producing the racemic N-carbamoyl-α-methylcysteine derivative in a small number of steps and high yield has not yet been established.

A known example of a general process for producing a racemic N-carbamoyl-α-disubstituted amino acid comprises converting an acetone derivative to racemic 5,5-disubstituted hydantoin by the Bucherer method, hydrolyzing the racemic 5,5-disubstituted hydantoin to produce a racemic α-disubstituted amino acid derivative (Agr. Biol. Chem., 1971, 35, 53-58), and then N-carbamoylating the derivative by treatment with potassium cyanate. However, in this method, the ureylene group (—NHCONH—) of the racemic 5,5-disubstituted hydantoin cannot be effectively used as the ureido group (carbamoylamino group: —NHCONH$_2$) of the racemic N-carbamoyl-α-disubstituted amino acid derivative. Also, the method requires the three steps and is thus inefficient.

On the other hand, as a method for producing a carbamoyl compound without passing through an amino acid produced by hydrolysis of hydantoin, a method of hydrolyzing with calcium hydroxide used as a base is known (U.S. Pat. No. 5,338,859). However, as a result of production of a racemic N-carbamoyl-α-methylcysteine derivative according to this method, the inventors found that the target compound can be obtained in only 25% yield. Namely, a process for producing a racemic N-carbamoyl-α-disubstituted amino acid derivative, particularly a racemic N-carbamoyl-α-methylcysteine derivative, in a small number of steps and high yield has not yet been established.

On the other hand, with respect to enzymatic optical resolution of a racemic N-carbamoyl-α-methylcysteine derivative, Japanese Unexamined Patent Application Publication No. 1-124398 discloses a resolution process in which a racemic N-carbamoyl-amino acid derivative is stereoselectively cyclized by treatment with hydantoinase. However, the possibility of reaction of an N-carbamoyl-α-methylcysteine derivative is neither disclosed nor suggested.

SUMMARY OF THE INVENTION

In consideration of the above-described situation, an object of the present invention is to provide an industrially practical process capable of simply producing an optically active L- or D-α-methylcysteine derivative or its salts, which is useful as a pharmaceutical intermediate, from readily available, inexpensive raw materials.

As a result of intensive research in consideration of the above-described situation, the inventors found a process for producing an α-methyl-L-cysteine derivative or its salt, the process comprising treating a racemic N-carbamoyl-α-methylcysteine derivative or its salt with a hydantoinase to selectively cyclize the D-isomer and form a D-5-methyl-5-thiomethylhydantoin derivative or its salt and an N-carbamoyl-α-methyl-L-cysteine derivative or its salt, and then decarbamoylating the N-carbamoyl-α-methyl-L-cysteine derivative or its salt and deprotecting the sulfur atom.

The inventors also found a process for producing an α-methyl-D-cysteine derivative or its salt, the process comprising hydrolyzing a D-5-methyl-5-thiomethylhydantoin derivative or its salts and deprotecting the sulfur atom. Furthermore, the inventors established a simple method for effectively producing a racemic N-carbamoyl-α-methylcysteine derivative used as a raw material of the above-described processes. These processes resulted in the completion of the present invention.

Namely, the present invention relates to a process for producing a D-5-methyl-5-thiomethylhydantoin derivative represented by formula (2) or its salt:

(wherein R$^1$ represents a substituted or unsubstituted alkyl group having 1 to 20 carbon atoms, a substituted or unsubstituted aralkyl group having 7 to 20 carbon atoms, or a substituted or unsubstituted aryl group having 6 to 20 carbon atoms); and an N-carbamoyl-α-methyl-L-cysteine derivative represented by formula (3) or its salt:

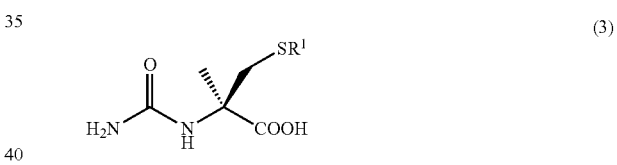

(wherein R$^1$ represents the same as the above), the process comprising treating a racemic N-carbamoyl-α-methylcysteine derivative represented by formula (1) or its salt with a hydantoinase to selectively cyclize the D-isomer:

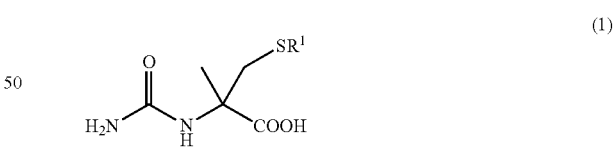

(wherein R$^1$ represents the same as the above).

Also, the present invention relates to a process for producing an α-methyl-L-cysteine derivative represented by formula (4) or its salt:

(wherein R$^2$ represents a hydrogen atom or R$^1$ as described above), the process comprising decarbamoylating the N-carbamoyl-α-methyl-L-cysteine derivative represented by formula (3) or its salts, and, if required, deprotecting the sulfur atom.

Furthermore, the present invention relates to a process for producing an α-methyl-L-cysteine represented by formula (5) or its salt:

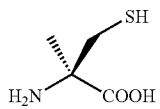
(5)

the process comprising treating an N-carbamoyl-α-methyl-L-cysteine derivative represented by formula (3) or its salt in which R¹ is a tertiary alkyl group having 4 to 15 carbon atoms with an acid to simultaneously perform decarbamoylation and deprotection of the sulfur atom.

Furthermore, the present invention relates to a process for producing L-5-methyl-5-thiomethylhydantoin represented by formula (6) or its salt:

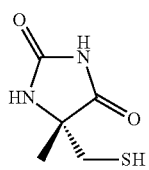
(6)

the process comprising cyclizing N-carbamoyl-α-methyl-L-cysteine derivative (3) or its salt and deprotecting the sulfur atom thereof.

Furthermore, the present invention relates to a process for producing L-5-methyl-5-thiomethylhydantoin (6) or its salt, the process comprising cyclizing N-carbamoyl-α-methyl-L-cysteine derivative (3) or its salt to produce a L-5-methyl-5-thiomethylhydantoin derivative represented by formula (7) or its salt:

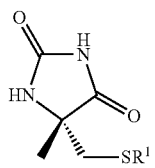
(7)

(wherein R¹ represents the same as the above), and then treating the derivative or its salt with an acid to deprotect the sulfur atom thereof.

Furthermore, the present invention relates to a process for producing an α-methyl-D-cysteine derivative represented by formula (8) or its salt:

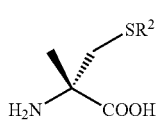
(8)

(wherein R² represents the same as the above), the process comprising hydrolyzing D-5-methyl-5-thiomethylhydantoin derivative (2) or its salt, and, if required, deprotecting the sulfur atom thereof.

Furthermore, the present invention relates to a process for producing α-methyl-D-cysteine represented by formula (9) or its salt:

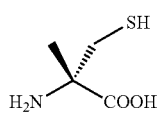
(9)

the process comprising treating the compound represented by formula (2) in which R¹ is a tertiary alkyl group having 4 to 15 carbon atoms with an acid to simultaneously perform hydrolysis reaction and deprotection of the sulfur atom.

Furthermore, the present invention relates to a process for producing D-5-methyl-5-thiomethylhydantoin represented by formula (11) or its salt:

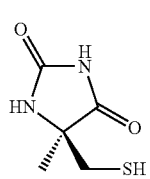
(11)

the process comprising carbamoylating an α-methyl-D-cysteine derivative represented by formula (8) or its salt in which R² is the same as R¹ to produce an N-carbamoyl-α-methyl-D-cysteine derivative represented by formula (10) or its salt:

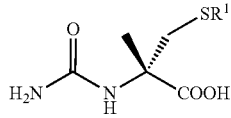
(10)

(wherein R¹ represents the same as the above), and then cyclizing the derivative or its salt and deprotecting the sulfur atom thereof.

Furthermore, the present invention relates to a process for producing D-5-methyl-5-thiomethylhydantoin represented by formula (11) or its salt, the process comprising treating the compound represented by formula (2) with an acid to deprotect the sulfur atom. The optically active 5-methyl-5-thiomethylhydantoin derivative or its salt can be easily converted to optically active α-methylcysteine by hydrolysis, and as well as optically active α-methylcysteine, the optically active 5-methyl-5-thiomethylhydantoin derivative or its salt can be suitably used as a synthetic intermediate for pharmaceuticals and the like.

Furthermore, the present invention relates to a process for crystallizing optically active α-methylcysteine or its salt, the process comprising crystallizing from an aqueous solution of an optically active α-methylcysteine or its salt in the presence of an organic solvent.

Furthermore, the present invention relates to a process for producing a racemic N-carbamoyl-α-amino acid derivative represented by formula (13) or its salt:

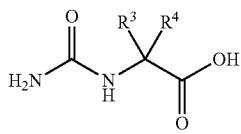

(13)

(wherein $R^3$ and $R^4$ independently represent a substituted or unsubstituted alkyl group having 1 to 20 carbon atoms, a substituted or unsubstituted aralkyl group having 7 to 20 carbon atoms, or a substituted or unsubstituted aryl group having 6 to 20 carbon atoms), particularly a racemic N-carbamoyl-α-methylcysteine derivative represented by formula (1) or its salt, the process comprising hydrolyzing, with an organic base or an alkali metal hydroxide, a racemic 5,5-disubstituted hydantoin derivative represented by formula (12) or its salt:

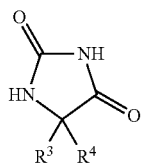

(12)

(wherein $R^3$ and $R^4$ represent the same as the above), particularly a racemic 5-methyl-5-thiomethylhydantoin derivative represented by formula (14) or its salt:

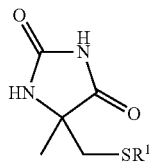

(14)

(wherein $R^1$ represents the same as the above).

Furthermore, the present invention relates to a racemic N-carbamoyl-α-methylcysteine derivative represented by formula (1) or its salt; an L- or D-optically active N-carbamoyl-α-methylcysteine derivative represented by formula (3) or (10) or its salt; a D- or L-optically active 5-methyl-5-thiomethylhydantoin derivative represented by formula (2) or (7) or its salt in which $R^1$ is a tertiary alkyl group having 4 to 15 carbon atoms; an L- or D-optically active α-methylcysteine derivative represented by formula (4) or (8) or its salt in which $R^2$ is a substituted or unsubstituted alkyl group having 1 to 20 atoms, a substituted or unsubstituted aralkyl group having 7 to 20 carbon atoms, or a substituted or unsubstituted aryl group having 6 to 20 carbon atoms; and an L- or D-optically active 5-methyl-5-thiomethylhydantoin represented by formula (6) or (11) or its salt.

DETAILED DISCLOSURE OF THE INVENTION

The present invention will be described in detail below. First, compounds of the present invention will be described.

In racemic N-carbamoyl-α-methylcysteine derivative (1) used in the present invention, $R^1$ represents a substituted or unsubstituted alkyl group having 1 to 20 carbon atoms, a substituted or unsubstituted aralkyl group having 7 to 20 carbon atoms, or a substituted or unsubstituted aryl group having 6 to 20 carbon atoms.

Examples of an alkyl group having 1 to 20 carbon atoms include linear alkyl groups such as a methyl group, an ethyl group, a n-propyl group, and a n-butyl group; and branched alkyl groups such as an isopropyl group, an isobutyl group, a tert-butyl group, a neopentyl group, a tert-pentyl group, and a tert-hexyl group. An alkyl group having 1 to 10 carbon atoms is preferred.

Examples of an aralkyl group having 7 to 20 carbon atoms include a benzyl group, a p-methoxybenzyl group, a phenethyl group, and a naphthylmethyl group. An aralkyl group having 7 to 15 carbon atoms is preferred.

Examples of an aryl group having 6 to 20 carbon atoms include a phenyl group and a naphthyl group. An aryl group having 6 to 15 carbon atoms is preferred.

Each of the alkyl group, aralkyl group, and aryl group may be unsubstituted or substituted. Examples of a substituent include an amino group, a hydroxyl group, an aryl group, an alkanoyl group, an alkenyl group, an alkynyl group, an alkoxy group, a nitro group, and halogen atoms.

Examples of an aryl group as the substituent include aryl groups each having 6 to 15 carbon atoms, such as a phenyl group, a naphthyl group, a p-methylphenyl group, a m-methylphenyl group, and an o-methylphenyl group. Examples of an alkanoyl group include alkanoyl groups each having 2 to 10 carbon atoms, such as an acetyl group, a propanoyl group, and a butanoyl group. Examples of an alkenyl group include alkenyl groups each having 2 to 10 carbon atoms, such as an ethenyl group and a propenyl group. Examples of an alkynyl group include alkyl groups each having 2 to 10 carbon atoms, such as an ethynyl group and a propynyl group. Examples of an alkoxy group include alkoxy groups each having 1 to 10 carbon atoms, such as a methoxy group, an ethoxy group, a n-propoxy group, and an isopropoxy group. Examples of halogen atoms include a fluorine atom, a chlorine atom, a bromine atom, and an iodine atom.

From the viewpoint of the ease of deprotection and the reactivity of stereoselective cyclization reaction with hydantoinase, $R^1$ is preferably a substituted or unsubstituted tertiary alkyl group having 4 to 15 carbon atoms. Specifically, $R^1$ is a tert-butyl group, a tert-pentyl group, or a tert-hexyl group, and preferably a tert-butyl group.

In racemic N-carbamoyl-α-amino acid derivative (13), $R^3$ and $R^4$ independently represent a substituted or unsubstituted alkyl group having 1 to 20 carbon atoms, a substituted or unsubstituted aralkyl group having 7 to 20 carbon atoms, or a substituted or unsubstituted aryl group having 6 to 20 carbon atoms. Examples of an alkyl group having 1 to 20 carbon atoms, an aralkyl group having 7 to 20 carbon atoms, and an aryl group having 6 to 20 carbon atoms include the same groups as those described above for $R^1$.

The alkyl group, aralkyl group, and aryl group may be unsubstituted or substituted. Examples of the substituent include the same as those described above for $R^1$, and substituted thio groups represented by formula (15):

$$-SR^1 \qquad (15)$$

wherein $R^1$ represents the same as the above. Preferred examples of $R^1$ in formula (15) include the same as described above.

In order to prepare compound (13) by hydrolyzing corresponding hydantoin as described below, each of $R^3$ and $R^4$ is preferably a substituted or unsubstituted alkyl group having 1 to 6 carbon atoms from the viewpoint of reactivity of hydrolysis reaction. Examples of such an alkyl group include a methyl group, an ethyl group, a propyl group, a n-butyl group, a n-pentyl group, and a n-hexyl group. More preferably, at least one of $R^3$ and $R^4$ is a methyl group. When one of $R^3$ and $R^4$ is a methyl group, and the other is a methyl group substituted by substituted thio group (15), of course, compound (13) corresponds to compound (1).

Racemic N-carbamoyl-α-methylcysteine derivative (1) and racemic N-carbamoyl-α-amino acid derivative (13) may be salts with a base. The salts with a base are not particularly limited, but examples of the salts include salts with alkali metal hydroxides (sodium hydroxide, potassium hydroxide, lithium hydroxide, and the like); and salts with alkaline earth metal hydroxides (calcium hydroxide, magnesium hydroxide, and the like). Salts with sodium hydroxide and potassium hydroxide are preferred.

In the racemic optically active 5-methyl-5-thiomethylhydantoin derivative represented by formula (2), (7), or (14), $R^1$ is defined as described above for the compound represented by formula (1).

In the racemic 5,5-disubstituted hydantoin derivative represented by formula (12), $R^3$ and $R^4$ are defined as described above for the compound represented by formula (13). Of course, when one of $R^3$ and $R^4$ is a methyl group, and the other is a methyl group substituted by substituted thio group (15), compound (12) corresponds to compound (14).

The 5,5-disubstituted hydantoin derivatives may be salts with a base formed at the imido groups of the hydantoin rings. The salts are not particularly limited, but examples of the salts include salts with alkali metal hydroxides (sodium hydroxide, potassium hydroxide, lithium hydroxide, and the like); and salts with alkaline earth metal hydroxides (calcium hydroxide, magnesium hydroxide, and the like). Salts with sodium hydroxide and potassium hydroxide are preferred.

In the optically active N-carbamoyl-α-methylcysteine derivative represented by formula (3) or (10), $R^1$ represents the same as the above. The optically active N-carbamoyl-α-methylcysteine derivatives may be salts, and examples of the salts include the same as described above for the compound represented by formula (1).

In the optically active α-methylcysteine derivative represented by formula (4) or (8), $R^2$ represents $R^1$ or a hydrogen atom. The $R^1$ represents a substituted or unsubstituted alkyl group having 1 to 20 atoms, a substituted or unsubstituted aralkyl group having 7 to 20 carbon atoms, or a substituted or unsubstituted aryl group having 6 to 20 carbon atoms, and defined as described above for the compound represented by formula (1). The optically active α-methylcysteine derivatives may be salts with an acid or a base. Examples of an acid include hydrohalic acids (hydrochloric acid, hydrobromic acid, and hydrofluoric acid), sulfonic acids (methanesulfonic acid, benzenesulfonic acid, p-toluenesulfonic acid, and the like), sulfuric acid, nitric acid, and carboxylic acids (formic aid, acetic acid, propionic acid, oxalic acid, trifluoroacetic acid, and the like). Examples of a base include organic bases (ammonia, triethylamine, aniline, pyridine, and the like), alkali metal hydroxides (sodium hydroxide, potassium hydroxide, lithium hydroxide, and the like), and alkaline earth metal hydroxides (calcium hydroxide, magnesium hydroxide, and the like).

The optically active 5-methyl-5-thiomethylhydantoin represented by formula (6) or (11) may be a salt. Examples thereof include the same as those described above for the compound represented by formula (1).

A process for producing the compounds represented by formula (1) and (13) will be described in detail below. Racemic N-carbamoyl-α-amino acid derivative (13) or its salt can be produced by hydrolysis of the racemic 5,5-disubstituted hydantoin derivative represented by formula (12) or its salt with an organic base or an alkali metal hydroxide.

Racemic 5,5-disubstituted hydantoin derivative (12) or its salt used as a raw material can be synthesized from a corresponding ketone by the Bucherer method well known to persons skilled in the art.

In this method, hydrolysis is performed using a base such as an organic base or an alkali metal hydroxide. The organic base is not particularly limited, but examples of the organic base include methylamine, dimethylamine, trimethylamine, ethylamine, diethylamine, triethylamine, diisopropylethylamine, pyridine, and aniline. These organic bases may be used alone or in a mixture of two or more.

Examples of the alkali metal hydroxides include lithium hydroxide, sodium hydroxide, potassium hydroxide, and cesium hydroxide. These alkali metal hydroxides may be used alone or in a mixture of two or more.

In view of yield and economics, the base used in hydrolysis is preferably an alkali metal hydroxide, and more preferably sodium hydroxide or potassium hydroxide.

Although the amount of the base used is not particularly limited, the amount of the base is preferably 1 to 10 molar equivalents, and more preferably 2 to 5 molar equivalents, based on the amount of the substrate used.

As a reaction solvent, water only may be used, or a mixture of water and an organic solvent may be used.

Although the organic solvent mixed with water to be used as the solvent is not particularly limited, examples of the organic solvent include hydrocarbon solvents, ester solvents, ether solvents, alcoholic solvents, nitrile solvents, and amide solvents. Hydrocarbon solvents are preferred.

The hydrocarbon solvents are not particularly limited. Examples of the hydrocarbon solvents include toluene, benzene, xylene, hexane, cyclohexane, and heptane. These solvents may be used alone or in a mixture of two or more at any desired ratio. Among these solvents, toluene is preferred.

Examples of the ester solvents include ethyl formate, methyl acetate, ethyl acetate, isopropyl acetate, and methyl propionate.

Examples of the ether solvents include diethyl ether, tetrahydrofuran, 1,4-dioxane, and methyl tert-butyl ether.

Examples of the alcoholic solvents include methanol, ethanol, 1-propanol, isopropanol, 1-butanol, and 2-butanol.

Examples of the nitrile solvents include acetonitrile and propionitrile.

Examples of the amide solvents include dimethylformamide and dimethylacetamide.

The amount of water used for reaction is preferably 0.1 to 100 times the weight of the substrate used. In view of yield and volumetric efficiency, the amount of water is more preferably 0.1 to 10 times, and most preferably 0.2 to 3 times, the weight of the substrate used.

When the amount of the water used is 0.2 to 3 times the weight of the substrate, and the amount of the base used is 2 to 5 molar equivalents relative to the substrate used, the reaction proceeds in the highest yield.

The reaction temperature depends on the type of the substrate used, and the amounts of the materials used, and thus cannot be determined unconditionally. However, the reaction temperature can be selected from 50° C. to 150° C., and it is preferably 80° C. to 110° C., and more preferably 85° C. to 100° C.

The reaction time depends on the type of the substrate used, the amounts of the materials used, and the reaction temperature, and thus cannot be determined unconditionally. However, the reaction time is preferably 1 to 50 hours, and more preferably 2 to 24 hours for producing the product in high yield.

As a post-treatment after the reaction, the reaction product may be directly used in a next reaction, or may be subjected to isolation by extraction and purification after neutralization with an acid. Alternatively, the reaction mixture may be filtered to isolate the target compound.

Similarly, the compound represented by formula (1) can be synthesized by producing the racemic 5-methyl-5-thiomethylhydantoin derivative represented by formula (14) from a thioacetone derivative by the Bucherer method, and then hydrolyzing the derivative represented by formula (14).

Description will now be made of a process in which racemic N-carbamoyl-α-methylcysteine derivative (1) or its salt is subjected to D-selective cyclization reaction using hydantoinase to synthesize D-5-methyl-5-thiomethylhydantoin derivative (2) or its salt and N-carbamoyl-α-methyl-L-cysteine derivative (3) or its salt.

The hydantoinase is an enzyme having an activity to hydrolyze a 5-substituted hydantoin derivative or its salt to produce an N-carbamoyl-α-amino acid derivative. It is generally known that this enzyme produces a 5-substituted hydantoin derivative by cyclization of an N-carbamoyl-α-amino acid derivative in a reverse reaction of hydrolysis (Japanese Unexamined Patent Application Publication No. 1-1243989).

In the present invention, hydantoinase derived from plants, animals, or microorganisms may be used as the hydantoinase catalyzing the D-stereo-selective cyclization reaction. Among them, hydantoinase derived from microorganisms is preferably used for industrial application. Any microorganisms can be used as an enzyme source as long as the microorganisms have the ability of producing the enzyme. Examples of the microorganisms include the known microorganisms below which are capable of producing the enzyme.

Examples of the microorganisms include bacteria of the genera *Acetobacter, Achromobacter, Aerobacter, Agrobacterium, Alcaligenes, Arthrobacter, Bacillus, Brevibacterium, Corynebacterium, Enterobacter, Erwinia, Escherichia, Klebsiella, Microbacterium, Micrococcus, Protaminobacter, Proteus, Pseudomonas, Sartina, Serratia, Xanthomonas, Aeromonas, Flavobacterium*, and *Rhizobium*; actinomyces of the genera *Actinomyces, Mycobacterium, Nocardia, Streptomyces, Actinoplanes*, and *Rhodococcus*; molds of the genera *Aspergillus, Paecilomyces*, and *Penicillium*; and yeasts of the genera *Candida, Phichia, Rhodotorula*, and *Torulopsis*.

Preferably, an enzyme derived from microorganisms of the genus *Agrobacterium, Bacillus, Pseudomonas*, or *Rhizobium* is used.

More preferably, an enzyme derived from *Agrobacterium* sp. KNK712 (FERM BP-1900), *Bacillus* sp. KNK245 (FERN BP-4863), *Pseudomonas putida* IFO12996, *Pseudomonas* sp. KNK003A (FERN BP-3181) or *Rhizobium* sp. KNK1415 is used.

The *Agrobacterium* sp. KNK712, *Bacillus* sp. KNK245, and *Pseudomonas* sp. KNK003A are deposited as international deposits according to the Butapest Treaty in International Patent Organism Depositary, National Institute of Advanced Industrial Science and Technology, AIST Tsukuba Central 6, 1-1, Higashi 1-chome, Tsukuba-shi, Ibaraki-ken, Japan with accession number FERM BP-1900 on May 31, 1988, with accession number FERN BP-4863 on Nov. 2, 1994, and with accession number FERN BP-3181 on Dec. 1, 1990, respectively.

The microorganisms may be a wild strain or a variant with hydantoinase activity increased by mutation. Alternatively, the microorganisms may be transformed microorganisms produced by a gene recombination method or the like so as to produce hydantoinase derived from the microorganisms with high efficiency.

In a method for forming the transformed microorganisms capable of producing hydantoinase with high efficiency, a hydantoinase gene is cloned from a strain exhibiting hydantoinase activity, and an appropriate recombinant plasmid vector is formed and used for transformation of proper host cells to produce the transformed microorganisms, as described in, for example, WO96/20275. The recombinant DNA technology is well known in this field, and described in, for example, Molecular Cloning 2nd Edition (Cold Spring Harbor Laboratory Press, 1989), Current Protocols in Molecular Biology (Greene Publishing Associates and Wiley-Interscience).

Examples of the transformed microorganisms capable of producing hydantoinase with high efficiency include the microorganisms described in WO96/20275, such as *Escherichia coli* HB101 pTH104 (FERN BP-4864) containing a hydantoinase gene derived from *Bacillus* sp. KNK245 (FERN BP-4863), *Escherichia coli* HB101 pAH1043 (FERN BP-4865) containing a hydantoinase gene derived from *Agrobacterium* sp. KNK712 (FERN BP-1900), and *Escherichia coli* HB101 pPHD301 (FERN BP-4866) containing a hydantoinase gene derived from *Pseudomonas* sp. KNK003A (FERN BP-3181).

The *Escherichia coli* HB101 pTH104, *Escherichia coli* HB101 pAH1043, and *Escherichia coli* HB101 pPHD301 are deposited as international deposits according to the Butapest Treaty in International Patent Organism Depositary, National Institute of Advanced Industrial Science and Technology, AIST Tsukuba Central 6, 1-1, Higashi 1-chome, Tsukuba-shi, Ibaraki-ken, Japan on Nov. 2, 1994 with accession number FERN BP-4864, accession number FERN BP-4865 and accession number FERN BP-4866, respectively.

When the hydantoinase is produced from the microorganisms exhibiting hydantoinase activity or the transformed microorganisms, culture may be performed using an ordinary nutrient medium, and, if required, enzyme induction treatment may be performed, as described in, for example, WO96/20275. The enzyme induction can be performed by, for example, adding uracil to the culture medium.

In the present invention, the hydantoinase produced from the microorganisms can be used directly as an enzyme or used in the form of microorganisms having activity for the enzyme or a treatment product thereof. Examples of the treatment product of microorganisms include a crude extract, lyophilized organisms prepared from cultured cells, acetone-dried cells, and disrupted products of these cells.

The enzyme may be immobilized in the form of an enzyme or cells by a known means and used as an immobilized enzyme. When the enzyme is stabilized by immobilization, enzymatic reaction can be performed in a severer temperature region to effectively accelerate the reaction. Furthermore, it is possible to expect the advantage that the production cost can be decreased due to repeatable use of the enzyme and simplification of the production process.

The immobilization can be performed by a method well known to persons skilled in the art, such as a cross-linking method, a covalent bonding method, a physical adsorption method, or an inclusion method. Examples of a support suitably used for immobilizing the enzyme include phenol-formaldehyde anion exchange resins such as Duolite A-568 and DS17186 (Rohm and Haas Co.: trademark), and anion exchange resins comprising polystyrene resins having amine-, ammonium salt- or diethanolamine-type functional groups, such as Amberlite IRA935, IRA945, and IRA901 (Rohm and Haas Co.: trademark), Lewatit OC1037 (Bayer Corp.: trademark), and Diaion EX-05 (Mitsubishi Chemical Corporation: trademark). As the support, DEAE-celluose can also be used.

The immobilized enzyme is preferably produced by the method described in, for example, WO96/20275. In this method, cells are collected from a culture solution of a strain having hydantoinase activity and then disrupted by ultrasonic waves or the like, and, for example, anion exchange resin Duolite A-568 is added to the resultant enzyme solution, followed by stirring for adsorption of the enzyme. In order to further improve stability, for example, a cross-linking agent such as glutaraldehyde may be added to the resin having the enzyme adsorbed thereon, and the resultant mixture may be subjected to cross-linking treatment by stirring. After these treatments, the resin is filtered off and then washed to produce immobilized hydantoinase.

In the present invention, the enzymatic reaction can be performed by the following method: The racemic N-carbamoyl-α-methylcysteine derivative represented by formula (1) or its salt is used as a substrate and subjected to reaction in an aqueous medium in the presence of the hydantoinase. The concentration of the substrate charged is 0.1% (w/v) to 90% (w/v), and preferably 1% (w/v) to 50% (w/v). The substrate is subjected to the reaction in a dissolved or suspended state by standing or stirring for a while at a reaction temperature properly adjusted to 10° C. to 80° C., preferably 20° C. to 60° C., and a pH kept at 4 to 9, preferably 5 to 8. Alternatively, the substrate can be continuously added. The reaction can be performed in a batch system or a continuous system. In the present invention, the reaction can be performed with the immobilized enzyme, a membrane reactor, and the like.

Examples of the aqueous medium include water, buffers (for example, a phosphate buffer, a Tris buffer, and a carbonate buffer), and solvents each containing such a buffer and a water-soluble organic solvent (for example, ethanol, methanol, or acetonitrile). The aqueous medium may be combined with an organic solvent (for example, ethyl acetate, butyl acetate, toluene, chloroform, or n-hexane) insoluble in water to form a two-phase system. If required, an antioxidant, a surfactant, a coenzyme, a metal, and the like can be further added to the medium.

As the result of the above-described reaction, only the D-isomer of racemic N-carbamoyl-α-methylcysteine derivative (1) or its salt is cyclized to be converted to D-5-methyl-5-thiomethylhydantoin derivative (2) or its salt and N-carbamoyl-α-methyl-L-cysteine derivative (3) or its salt.

The produced N-carbamoyl-α-methyl-L-cysteine derivative (3) or its salt may be subjected to decarbamoylation reaction in the form of the reaction solution, or may be isolated and purified by a conventional separation method such as extraction, concentration, crystallization, or column chromatography, or combination thereof.

For example, when N-carbamoyl-S-tert-butyl-α-methylcysteine having a tert-butyl group at $R^1$ in formula (1) is used as the substrate of D-selective cyclization reaction with the hydantoinase, D-5-methyl-5-tert-butylthiomethylhydantoin precipitated as an insoluble substance after the reaction can be easily removed by filtration.

In this case, the filtrate containing the resultant N-carbamoyl-α-methyl-L-cysteine may be used in a next step directly or after purification. In the purification, the filtrate is controlled to acid pH to precipitate crystals, and then filtered to obtain the target compound.

The D-5-methyl-5-tert-butylthiomethylhydantoin precipitated as an insoluble substance may be used directly in a next step or used in the form of an aqueous alkali solution in a next step. Alternatively, the aqueous alkali solution may be neutralized to crystallize the D-5-methyl-5-tert-butylthiomethylhydantoin. Any one of these methods may be used.

Description will now be made of a process for producing the α-methyl-L-cysteine derivative represented by formula (4) or its salt, the process comprising decarbamoylating N-carbamoyl-α-methyl-L-cysteine derivative (3) or its salt, and, if required, deprotecting the sulfur atom.

The protecting group of the sulfur atom is selected from the groups described above as $R^1$. In the deprotection, decarbamoylation (deprotection of the amino group) and deprotection of the sulfur atom may be simultaneously performed. Alternatively, one of the deprotection steps may be first performed, and then the other step may be performed to remove the remaining protecting group. The deprotection method may be appropriately selected according to the protecting group and the purpose.

First, the method of simultaneously performing decarbamoylation and deprotection of the sulfur atom will be described. As a result of intensive research, the inventors found that when a tertiary alkyl group having 4 to 15 carbon atoms, such as a tert-butyl group, is used as the protecting group ($R^1$) of the sulfur atom, decarbamoylation (deprotection of the amino group) and deprotection of the sulfur atom can be simultaneously performed in one step by treating N-carbamoyl-α-methyl-L-cysteine derivative (3) or its salt with an acid.

Examples of the acid used in this method include hydrochloric acid, sulfuric acid, hydrobromic acid, nitric acid, acetic acid, and trifluoroacetic acid. Any one of these acids may be used alone, or at least two of the acids may be mixed at any desired ratio. From the viewpoint of reactivity and economics, hydrochloric acid or hydrobromic aid is preferred, and hydrochloric acid is more preferred. As hydrochloric acid or hydrobromic acid, commercially available concentrated hydrochloric acid or hydrobromic acid can be used, and such an acid can also be used as the reaction solvent. Although water or an organic solvent may be added, the acid is preferably also used as the reaction solvent from the viewpoint of reactivity.

With respect to the reaction conditions, for example, when N-carbamoyl-S-tert-butyl-α-methylcysteine having a tert-butyl group as the protecting group of the sulfur atom is treated with hydrochloric acid to produce α-methylcysteine hydrochloride in one step, the reaction temperature is preferably 70° C. to 180° C., and more preferably 90° C. to 150° C., and the reaction time is preferably about 2 to 4 days, for example, at 100° C. to 110° C. and atmospheric pressure. The reaction can be performed using a pressure-resisting reactor at a higher temperature to reduce the reaction time.

Next, description will be made of a process for producing α-methyl-L-cysteine represented by formula (5) or its salt, the process comprising decarbamoylating N-carbamoyl-α-methyl-L-cysteine derivative (3) or its salt to produce the α-methyl-L-cysteine derivative represented by formula (4) or its salt in which $R^2$ is the same as $R^1$ in formula (1), and then deprotecting the sulfur atom.

In this process, the decarbamoylation method is not particularly limited as long as the carbamoyl group can be removed. For example, a nitrous acid oxidation method, an alkaline hydrolysis method, or an acid hydrolysis method can be used. When the protecting group of the sulfur atom is a tertiary alkyl group such as a tert-butyl group, the acid hydrolysis method using hydrochloric acid, or the like tends to progress the deprotection of the sulfur atom. Therefore, when only decarbamoylation is desired, another method is preferably performed.

The nitrous acid oxidation method can use the reaction conditions generally used for decarbamoylation. For example, nitrous acid alone or a combination of a nitrite and an appropriate acid can be used. However, a combination of a nitrite and an acid is preferably used.

Examples of the nitrite include sodium nitrite, potassium nitrite, calcium nitrite, cesium nitrite, magnesium nitrite, and barium nitrite. Among these nitrites, potassium nitrite and sodium nitrite are preferred. As the acid combined with the nitrite, acetic acid, hydrochloric acid, sulfuric acid, and hydrobromic acid are preferred, and hydrochloric acid is particularly preferred. Although the solvent is not particularly limited, water or an alcohol (for example, methanol, ethanol, isopropanol, or the like) is preferably used from the viewpoint of solubility of the substrate.

The reaction temperature of the nitrous acid oxidation method is preferably in the range of −5° C. to 100° C., and more preferably in the range of 0° C. to 50° C. from the viewpoint of product stability and improvement in yield.

The alkali used in the alkaline hydrolysis method is not particularly limited. For example, sodium hydroxide, lithium hydroxide, potassium hydroxide, barium hydroxide, magnesium hydroxide, calcium hydroxide, and the like are preferred, and lithium hydroxide is more preferred.

The reaction temperature of alkaline hydrolysis is preferably in the range of −5° C. to 150° C., and more preferably in the range of 80° C. to 120° C. from the viewpoint of productivity and improvement in yield.

The compound represented by formula (4) in which $R^2$ is the same as $R^1$ in formula (1) may be used in a next step directly or after purification. For example, when $R^2$ is a tert-butyl group, purification can by performed by adding an acid to the reaction solution after the alkaline hydrolysis to decrease the pH of the solution. As a result, the α-methyl-L-cysteine derivative represented by formula (4) or its salt in which $R^2$ is a tert-butyl group can be obtained as crystals.

In this case, the alkali used for the alkaline hydrolysis is arbitrarily selected from sodium hydroxide, lithium hydroxide, potassium hydroxide, barium hydroxide, magnesium hydroxide, calcium hydroxide, and the like. Examples of the acid added to the reaction solution after the alkaline hydrolysis include hydrochloric acid, sulfuric acid, hydrobromic acid, nitric acid, acetic acid, and trifluoroacetic acid. Any one of these acids may be used alone, or two or more may be mixed at any desired ratio. However, a combination of lithium hydroxide used as the alkali and hydrochloric acid used as the acid is preferably used because an inorganic salt produced in neutralization has high solubility in water to facilitate desalting.

The term "neutralization" means that the pH of the reaction solution is adjusted to a crystallization region. In order to efficiently produce crystals of the α-methyl-L-cysteine derivative represented by formula (4) or its salt in which $R^2$ is a tert-butyl group, the upper limit of the pH is preferably 9.5 or less, and more preferably 7.0 or less, and the lower limit of the pH is generally 1.0 or more, preferably 2.0 or more, and more preferably 3.0 or more.

When deprotection of the sulfur atom is further required after the above-described decarbamoylation, for example, the sulfur atom can be deprotected under reaction conditions suitable for the protecting group directly using the reaction solution or after isolation of the α-methyl-L-cysteine derivative.

For example, when the protecting group is a tertiary alkyl group such as a tert-butyl group or the like, the sulfur atom can be deprotected by treatment with an acid. Examples of the acid include hydrochloric acid, sulfuric acid, hydrobromic acid, nitric acid, acetic acid, and trifluoroacetic acid. Any one of these acids may be used alone, or two or more may be mixed at any desired ratio. Among these acids, hydrochloric acid or hydrobromic acid is preferred, and hydrochloric acid is more preferred. As hydrochloric acid or hydrobromic acid, commercially available conc. hydrochloric acid or conc. hydrobromic acid can be used, and such an acid can also be used as the reaction solvent. Although water or an organic solvent may be added, the acid is preferably also used as the solvent from the viewpoint of reactivity. The reaction temperature is preferably 50° C. to 120° C., and more preferably 80° C. to 100° C.

Description will now be made of the process for producing α-methyl-L-cysteine (5) or its salt from the N-carbamoyl-α-methyl-L-cysteine derivative represented by formula (3) or its salt through L-5-methyl-5-thiomethylhydantoin (6) or its salt.

First, the method for performing sulfur atom deprotection and cyclization reaction of N-carbamoyl-α-methyl-L-cysteine derivative (3) or its salt in one step will be described. When the protecting group of the sulfur atom is a tertiary alkyl group such as a tert-butyl group, deprotection and cyclization can be simultaneously performed by treatment with an acid.

Examples of the acid include hydrochloric acid, sulfuric acid, hydrobromic acid, nitric acid, acetic acid, and trifluoroacetic acid. Any one of these acids may be used alone, or two or more may be mixed at any desired ratio. Among these acids, hydrochloric acid is preferred. As hydrochloric acid or hydrobromic acid, commercially available conc. hydrochloric acid or conc. hydrobromic acid can be used, and such an acid can also be used as the reaction solvent. Although water or an organic solvent may be added, the acid is preferably also used as the solvent from the viewpoint of reactivity.

Although the reaction temperature is not particularly limited, mild conditions are preferred for suppressing the hydrolysis of L-5-methyl-5-thiomethylhydantoin (6) or its salt. For example, the reaction may be performed in the range of 0° C. to 100° C., preferably 60° C. to 90° C., for several hours, and terminated when the major product is the desired compound.

Next, the method comprising synthesizing L-5-methyl-5-thiomethylhydantoin derivative (7) or its salt by cyclization and then deprotecting the sulfur atom will be described. When the protecting group of the sulfur atom is a tertiary alkyl group such as a tert-butyl group, cyclization is preferably performed by alkali treatment because deprotection of the sulfur atom proceeds when cyclization is performed with an acid.

The alkali used is not particularly limited, and examples of the alkali include sodium hydroxide, potassium hydroxide, lithium hydroxide, magnesium hydroxide, barium hydroxide, and calcium hydroxide. In view of availability and cost, sodium hydroxide, potassium hydroxide or lithium hydroxide is preferred.

The reaction temperature of cyclization is preferably 0° C. to 100° C., and more preferably 60° C. to 90° C. The solvent may comprise only water, or a mixture of water and an organic solvent. The solvent preferably comprises only water.

L-5-methyl-5-thiomethylhydantoin derivative (7) or its salt may be used in a next step directly or after extraction with an organic solvent or isolation by crystallization or the like.

The resultant derivative (7) or its salt can be further treated with an acid to advance deprotection of the sulfur atom, and thereby L-5-methyl-5-thiomethylhydantoin (6) or its salt can be produced.

Examples of the acid include hydrochloric acid, sulfuric acid, hydrobromic acid, nitric acid, acetic acid, and trifluoroacetic acid. Any one of these acids may be used alone, or two or more may be mixed at any desired ratio. In view of yield and cost, hydrochloric acid is preferred. The acid treatment can be preferably performed under the same conditions as those described above for performing deprotection and cyclization in one step.

L-5-methyl-5-thiomethylhydantoin (6) or its salt produced as described above can be converted to α-methyl-L-cysteine (5) or its salt by acid or alkaline hydrolysis. The hydrolysis with an acid is preferred.

Examples of the acid include hydrochloric acid, sulfuric acid, hydrobromic acid, nitric acid, acetic acid, and trifluoroacetic acid. Any one of these acids may be used alone, or two or more may be mixed at any desired ratio. Among these acids, hydrochloric acid or hydrobromic acid is preferred, and hydrochloric acid is more preferred. Preferred examples of the alkali include sodium hydroxide, potassium hydroxide, and lithium hydroxide.

Description will now be made of a process for producing α-methyl-D-cysteine or its salt by hydrolyzing D-5-methyl-5-thiomethylhydantoin derivative (2) or its salt, and then deprotecting the sulfur atom of the resultant α-methyl-D-cysteine derivative represented by formula (8) or its salt in which $R^2$ is the same as $R^1$ in formula (1).

The hydrolysis is usually performed with an alkali. The alkali used in the hydrolysis is not particularly limited, but examples of the alkali include sodium hydroxide, potassium hydroxide, lithium hydroxide, barium hydroxide, magnesium hydroxide, and calcium hydroxide. Among these alkalis, sodium hydroxide, potassium hydroxide, and lithium hydroxide are preferred. Particularly, lithium hydroxide is preferably used because an inorganic salt impurity produced in crystallization of the product after the reaction has high solubility in water.

The solvent may comprise only water or a mixture of water and an organic solvent, but the solvent preferably comprises only water.

The reaction temperature is preferably −5° C. to 150° C., and more preferably 80° C. to 120° C.

For example, when $R^2$ is a tert-butyl group, an acid is added to the reaction solution to decrease its pH after the hydrolysis reaction, and thereby the resulting α-methyl-S-tert-butyl-D-cysteine can be obtained as crystals.

The acid used is not particularly limited as long as the pH of the reaction solution can be decreased. Examples of the acid include hydrochloric acid, sulfuric acid, hydrobromic acid, nitric acid, acetic acid, and trifluoroacetic acid. Any one of these acids may be used alone, or two or more may be mixed at any desired ratio. Among these acids, hydrochloric acid is preferably used because when the hydrolysis is performed with lithium hydroxide, an inorganic salt impurity produced in neutralization has high solubility in water and is thus little mixed into the crystals.

The term "neutralization" means that the pH of the reaction solution is adjusted to a crystallization region. In order to efficiently produce crystals of the α-methyl-S-tert-butyl-D-cysteine, the upper limit of the pH is preferably 9.5 or less, and more preferably 7.0 or less, and the lower limit of the pH is 1.0 or more, preferably 2.0 or more, and more preferably 3.0 or more.

The resulting compound represented by formula (8) in which $R^2$ is the same as $R^1$ can be converted to α-methyl-D-cysteine (9) or its salt by deprotecting the sulfur atom. The deprotection method is selected according to the protecting group of the sulfur atom. When the protecting group is a tertiary alkyl group such as a tert-butyl group or the like, the deprotection can be easily performed by treatment with an acid.

Examples of the acid used in the method include hydrochloric acid, sulfuric acid, hydrobromic acid, nitric acid, acetic acid, and trifluoroacetic acid. Any one of these acids may be used alone, or two or more may be mixed at any desired ratio. From the viewpoint of reactivity and economics, hydrochloric acid or hydrobromic acid is preferred, and hydrochloric acid is more preferred. As hydrochloric acid or hydrobromic acid, commercially available conc. hydrochloric acid or conc. hydrobromic acid can be used, and such an acid can also be used as the reaction solvent. Although water or an organic solvent may be added, the acid is preferably also used as the solvent from the viewpoint of reactivity.

The reaction temperature is preferably 70° C. to 180° C., and more preferably 90° C. to 150° C.

Next, the method for performing sulfur atom deprotection and hydrolysis reaction of D-5-methyl-5-thiomethylhydantoin derivative (2) or its salt using an acid in one step will be described. For example, when $R^1$ in formula (2) is a tertiary alkyl group having 4 to 15 carbon atoms, such as a tert-butyl group, α-methyl-D-cysteine (9) or its salt can be obtained by treatment with an acid in one step.

Examples of the acid include hydrochloric acid, sulfuric acid, hydrobromic acid, nitric acid, acetic acid, and trifluoroacetic acid. Any one of these acids may be used alone, or two or more may be mixed at any desired ratio. Among these acids, hydrochloric acid or hydrobromic acid is preferred, and hydrochloric acid is more preferred. As hydrochloric acid or hydrobromic acid, commercially available conc. hydrochloric acid or conc. hydrobromic acid can be used, and such an acid can also be used as the reaction solvent. Although water or an organic solvent may be added, the acid is preferably also used as the solvent from the viewpoint of reactivity.

The reaction temperature is preferably 70° C. 180° C., and more preferably 90° C. to 150° C.

Next, description will be made of a process for producing α-methyl-D-cysteine (9) or its salt, the process comprising synthesizing D-5-methyl-5-thiomethylhydantoin (11) or its salt by deprotecting the sulfur atom of D-5-methyl-5-thiomethylhydantoin derivative (2) or its salt and then hydrolyzing the compound (11) or its salt.

First, the method of selectively deprotecting the sulfur atom of D-5-methyl-5-thiomethylhydantoin derivative (2) or its salt to produce D-5-methyl-5-thiomethylhydantoin (11) or its salt will be described. As described above, when the protecting group of the sulfur atom is a tertiary alkyl group such as a tert-butyl group, deprotection can easily be performed by treatment with an acid.

Examples of the acid include hydrochloric acid, sulfuric acid, hydrobromic acid, nitric acid, acetic acid, and trifluoroacetic acid. Any one of these acids may be used alone, or two or more may be mixed at any desired ratio. Among these acids, hydrochloric acid is preferred. As hydrochloric acid or hydrobromic acid, commercially available conc. hydrochloric acid or conc. hydrobromic acid can be used, and such an acid can also be used as the reaction solvent. Although water or an organic solvent may be added, the acid is preferably also used as the solvent from the viewpoint of reactivity.

The reaction conditions are not particularly limited as long as they are relatively mild for producing D-5-methyl-5-thiomethylhydantoin (11) with high selectivity while suppressing hydrolysis. However, the reaction may be performed at 100° C. or less for several hours, and terminated when the major product is the desired compound.

Next, D-5-methyl-5-thiomethylhydantoin (11) or its salt is hydrolyzed to produce α-methyl-D-cysteine (9) or its salt.

The hydrolysis may be either acid hydrolysis or alkaline hydrolysis. In the acid hydrolysis, examples of an acid include hydrochloric acid, sulfuric acid, hydrobromic acid, nitric acid, acetic acid, and trifluoroacetic acid. Any one of these acids may be used alone, or two or more may be mixed at any desired ratio. In view of reactivity and economics, hydrochloric acid or hydrobromic acid is preferred, and hydrochloric acid is more preferred. As hydrochloric acid or hydrobromic acid, commercially available conc. hydrochloric acid or conc. hydrobromic acid can be used, and such an acid can also be used as the reaction solvent. Although water or an organic solvent may be added, the acid is preferably also used as the solvent from the viewpoint of reactivity. The reaction temperature is preferably 70° C. to 180° C., and more preferably 90° C. to 150° C. The reaction time is preferably about 2 to 4 days, for example, at 100° C. to 110° C. and atmospheric pressure. The reaction can be performed using a pressure-resisting reactor at higher temperature to reduce the reaction time.

Next, description will be made of the process for producing D-5-methyl-5-thiomethylhydantoin (11) or its salt, the process comprising hydrolyzing D-5-methyl-5-thiomethylhydantoin derivative (2) or its salt to produce the α-methyl-D-cysteine derivative represented by formula (8) or its salt, converting the derivative (8) or its salt to N-carbamoyl-α-methyl-D-cysteine derivative (10) or its salt by carbamoylation, and then performing cyclization and deprotection of the sulfur atom.

In this process, D-5-methyl-5-thiomethyhydantoin derivative (2) or its salt can be converted to α-methyl-D-cysteine derivative (8) or its salt by the above-described method.

The carbamoylation of α-methyl-D-cysteine derivative (8) or its salt can be performed with an alkali metal cyanate and an acid. Examples of the alkali metal cyanate include potassium isocyanate, potassium cyanate, and sodium cyanate. Examples of the acid include hydrochloric acid, sulfuric acid, hydrobromic acid, nitric acid, acetic acid, and trifluoroacetic acid. By using these agents, the carbamoylation is performed under normal reaction conditions for carbamoylation (for example, 0° C. to 100° C. in an aqueous solvent).

The cyclization and sulfur atom deprotection of N-carbamoyl-α-methyl-D-cysteine derivative (10) or its salt can be performed by the same method as that described above for converting N-carbamoyl-α-methyl-L-cysteine derivative (3) or its salt to L-5-methyl-5-thiomethylhydantoin (6).

Next, a process for crystallizing optically active α-methylcysteine or its salt will be described in detail below. The optically active α-methylcysteine or its salt can be easily obtained by crystallization from an aqueous solution of the optically active α-methylcysteine or its salt in the presence of an organic solvent.

The optically active α-methylcysteine or its salt is not particularly limited, but optically active α-methylcysteine, a salt of optically active α-methylcysteine with an acid, and a salt of optically active α-methylcysteine with a base are given as examples. A salt with an acid is preferred. The optically active α-methylcysteine may be either the L-isomer or the D-isomer.

Examples of the acid of the acid salt include hydrohalic acids, sulfonic acids, sulfuric acid, nitric acid, and carboxylic acids. Among these acids, hydrohalic acids are preferred.

Examples of the hydrohalic acids include hydrochloric acid, hydrobromic acid, and hydrofluoric acid, and hydrochloric acid is preferred.

Examples of the sulfonic acids include methanesulfonic acid, benzenesulfonic acid, and p-toluenesulfonic acid. Examples of the carboxylic acids include formic acid, acetic acid, propionic acid, oxalic acid, and trifluoroacetic acid. Examples of the base of the base salt include ammonia, triethylamine, aniline, and pyridine.

The method for preparing the aqueous solution of the optically active α-methylcysteine or its salt is not particularly limited. For example, the aqueous solution can be prepared by appropriately converting or deprotecting the α-methylcysteine derivative or its salt produced by any one of the conventional processes 1) to 6), or a protected compound thereof. An aqueous solution of the compound produced by the method of the present invention may be used. Preferably, an aqueous solution of the optically active α-methylcysteine or its salt produced by the method of the present invention is used.

In the crystallization process, the aqueous solution of the optically active α-methylcysteine or its salt is concentrated in the presence of the organic solvent to remove water from the system and replace water by the organic solvent. Consequently, aggregation of the compound can be suppressed to produce slurry which can easily be taken out and filtered. The resulting slurry is filtered, and the residue is washed and then dried to produce the optically active α-methylcysteine or its salt as crystals.

When the crystallization process is carried out, the aqueous solution of the optically active α-methylcysteine or its salt may be preliminarily concentrated before the organic solvent is added. In this case, the aqueous solution is preferably concentrated until the concentration by weight of the compound is 10% by weight or more, more preferably 30% by weight or more.

The organic solvent used for replacement is not particularly limited, but the organic solvent is preferably azeotropic with water so that the water content at the azeotropic point is 5.0% by weight or more. The organic solvent more preferably has low or no compatibility with water.

Examples of the organic solvent having low or no compatibility with water include hydrocarbon solvents, ester solvents, and ether solvents. The hydrocarbon organic solvents are preferred from the viewpoint of low compatibility with water, low solubility of the optically active α-methylcysteine or its salt, and easy recovery and reuse of the solvent.

The hydrocarbon organic solvents are not particularly limited, but for example, toluene, benzene, xylene, hexane, cyclohexane, and heptane may be used alone or in a mixture of two or more. From the viewpoint of economics, toluene is preferred.

Examples of the ester solvents include ethyl acetate, isopropyl acetate, and isobutyl acetate.

Examples of the ether solvents include dipropyl ether, dibutyl ether, 1,4-dioxane, and methyl tert-butyl ether.

These solvents may be used alone or in a mixture of the same type or different types of solvents at any desired ratio.

The replacement by the organic solvent may be performed in one step or in a plurality of steps. The amount of the organic solvent used for the replacement depends on the type of the organic solvent, the degree of vacuum for concentration, and the internal temperature of the system, and thus cannot be determined unconditionally. For example, when toluene is used as the solvent, the amount of toluene charged each time is preferably 0.1 to 100 times, and more preferably 0.2 to 10 times the total weight of the aqueous solution.

After the organic solvent is added, water is removed from the system to crystallize the optically active α-methylcysteine or its salt. In this operation, the concentration of the solute, i.e., the concentration of the optically active α-methylcysteine or its salt, is 0.1 to 70% by weight, and preferably 1 to 70% by weight.

In the above-described operation, the amount of the water finally remaining after water removal from the system is preferably 100% by weight or less on the basis of the optically active α-methylcysteine or its salt. From the viewpoint of the properties of the resulting crystals, filterability, the rate of crystallization, and slurry fluidity, the water is preferably removed from the system until the water content becomes 40% by weight or less.

The evaporation rate in concentration depends on the ability of the apparatus used, and thus cannot be determined unconditionally. However, as the evaporation rate increases, bubbles significantly occur to worsen the fluidity of the resultant slurry and cause a tendency to aggregation. Therefore, the evaporation rate per unit evaporation area and unit time is preferably controlled to 1000 L/h·m$^2$ or less, more preferably 600 L/h·m$^2$ or less, further preferably 300 L/h·m$^2$ or less, and most preferably 100 L/h·m$^2$ or less.

In concentration after the addition of the organic solvent, the degree of vacuum is generally 500 mmHg or less, and preferably 200 mmHg or less. Although the lower limit is not particularly limited, the lower limit is generally 0.1 mmHg or more.

The concentration temperature depends on the degree of vacuum and the ability of the apparatus used, but the temperature is 0° C. to 150° C., preferably 10° C. to 100° C., and more preferably 30° C. to 70° C., for obtaining high-quality crystals easy to handle.

Next, detailed description will be made of a process for crystallizing the optically active α-methylcysteine or its salt from an aqueous solution thereof after an inorganic salt is removed. An organic solvent is added to the aqueous solution of the optically active α-methylcysteine or its salt, and then concentration is performed to remove water from the system and replace water by the organic solvent. In this operation, most of an insoluble inorganic salt is precipitated, and thus the inorganic salt can be removed by a method such as filtration or the like. The resultant filtrate is then mixed with a poor solvent, cooled or concentrated to obtain crystals of the optically active α-methylcysteine or its salt.

In the above-described operation, after the organic solvent is added and water is removed from the system, the amount of the finally remaining water is preferably 100% by weight or less on the basis of the optically active α-methylcysteine or its salt. From the viewpoint of the deposit of the inorganic salt to be removed, the water is preferably removed from the system until the water content becomes 40% by weight or less.

Although the type of the organic solvent used for replacement is not particularly limited, an organic solvent compatible with water is preferred from the viewpoint of the physical properties that the inorganic salt is slightly soluble or insoluble, and an optically active α-methylcysteine hydrochloride is soluble. More preferably, a single alcoholic solvent, a single ether solvent compatible with water, or a mixture thereof at any ratio is used.

Examples of the alcoholic solvent include methyl alcohol, ethyl alcohol, n-propyl alcohol, isopropyl alcohol, n-butyl alcohol, isobutyl alcohol, sec-butyl alcohol, and tert-butyl alcohol. Any one of these solvents may be used alone, or a mixture of two or more at any desired ratio may be used. However, isopropyl alcohol is preferred in view of the efficiency of dehydration, economics, decrease in side reactions such as esterification and the like.

Examples of the ether solvent compatible with water include diethyl ether, diisopropyl ether, tetrahydrofuran, 1,4-dioxane, and methyl tert-butyl ether. Any one of these solvents may be used alone, or a mixture of two or more at any desired ratio may be used. However, tetrahydrofuran is preferred in view of the efficiency of dehydration and economics.

The process for crystallizing the optically active α-methylcysteine or its salt from the filtrate obtained after the slightly soluble inorganic salt is removed is not particularly limited. For example, a general crystallization operation such as addition of a poor solvent, cooling, concentration, or the like can be carried out. Preferably, the method of adding a poor solvent is carried out.

The poor solvent is not particularly limited, but hydrocarbon solvents, ester solvents, ether solvents having no or low compatibility with water, and the like are given as examples. From the viewpoint of the deposit of crystals and crystal purity, hydrocarbon solvents and ester solvents are preferred, and hydrocarbon solvents are more preferred.

Although the hydrocarbon solvents are not particularly limited, examples of the hydrocarbon solvents include toluene, benzene, xylene, hexane, cyclohexane, and heptane. Among these solvents, toluene, xylene, hexane, and heptane are preferred, and toluene is more preferred.

Although the ester solvents are not particularly limited, examples of the ester solvents include methyl acetate, ethyl acetate, propyl acetate, methyl propionate, and ethyl propionate. Among these solvents, ethyl acetate is preferred.

Although the ether solvents having no or low compatibility with water are not particularly limited, examples of the ether solvents include dipropyl ether, dibutyl ether, 1,4-dioxane, and methyl tert-butyl ether.

These solvents may be used alone or in a mixture of the same type or different types of solvents at any desired ratio.

When the optically active α-methylcysteine or its salt is crystallized, the concentration of the compound depends on the temperature, the solvent ratio, and the like. However, the concentration of the compound is generally 0.1% by weight to 70% by weight, preferably 1% by weight to 70% by weight, and more preferably 2% by weight to 70% by weight, based on the whole weight of the solution.

The crystallization process of the present invention is capable of satisfactorily obtaining the optically active α-methylcysteine or its salt with high purity through industrially practical steps. The crystals produced by the crystallization method of the present invention contains a corresponding disulfide of the compound at a content of 1.0 mol % or less, preferably 0.5 mol % or less, and more preferably 0.1 mol % or less. A preferable form for obtaining the optically active α-methylcysteine or its salt having a low disulfide content is a salt with an acid, more preferably a salt with a hydrohalic acid, and most preferably a salt with hydrochloric acid.

BEST MODE FOR CARRYING OUT THE INVENTION

Although the present invention will be described in further detail below with reference to examples, the present invention is not limited to these examples.

Reference Example 1

Method for producing racemic 5-methyl-5-tert-butylthiomethylhydantoin

In a reactor provided with a nitrogen balloon, a 5 wt % aqueous sodium hydroxide solution (9.6 g, 12 mmol) and tert-butyl mercaptan (1.13 mL, 10 mmol) were mixed at 0° C., and the mixture was stirred for 10 minutes. Then, chloroacetone (0.79 mL, 10 mmol) was added to the mixture, and reaction was performed at room temperature for 2 hours. The reaction solution was light yellow and separated into two phases, A Dimroth condenser was attached to the reactor, and NaCN (588 mg, 12 mmol), $(NH_4)HCO_3$ (2.77 g, 35 mmol), and 28% ammonia water (3.1 mL) were added to the reactor to prepare a homogeneous solution. Then, the temperature was increased to 55° C. to 60° C. After stirring under heating for 6 hours, the solution was cooled to 0° C., and conc. hydrochloric acid was added to the reaction solution to control the pH to 7.0 to 7.6. The resulting white crystals were filtered off and analyzed by $^1$H NMR. As a result, it was found that the target compound (1.84 g, yield 84.8%) was produced.

Reference Example 2

Method for producing 5-(2-methoxyphenylmethyl)-5-methyl-hydantoin

First, 2-methoxyphenylacetone (16.4 g, 100 mmol) was mixed with 164 g or water, and NaCN (5.88 g, 120 mmol), $(NH_4)HCO_3$ (27.7 g, 350 mmol), and 27.7 g of 28% ammonia water were added to the resulting mixture. After stirring at 50° C. for 4 hours and at 60° C. for 12 hours, the mixture was allowed to cool down to 23° C., and then controlled to pH 7.5 by adding conc. hydrochloric acid. The precipitated solid was filtered off, washed with toluene, and dried under reduced pressure to obtain 22.10 g (yield 94.5%) of the title compound.

$^1$H NMR (300 MHz, $CDCl_3$) δ: 7.10-6.88 (m, 4H), 5.49 (brs, 1H), 3.86 (s, 3H), 3.20 (d, 1H), 2.97 (d, 1H), 1.49 (s, 3H)

Reference Example 3

Method for producing racemic N-carbamoyl-5-tert-butyl-α-methylcysteine

Racemic 5-methyl-5-thiomethylhydantoin (4.77 g, 22.1 mmol) was dissolved in a 10% aqueous sodium hydroxide solution (75 g), and the resultant solution was refluxed for 72 hours. After being allowed to cool down to room temperature, the reaction solution was sampled for confirming the production of racemic S-tert-butyl-α-methylcysteine by HPLC (column: COSMOSIL AR-II (produced by Nacalai Tesque Inc.), mobile phase: potassium dihydrogen phosphate-aqueous phosphate solution (pH 2.0)/acetonitrile=97/3, flow rate: 1.0 ml/min, detection wavelength: 210 nm, column temperature: 40° C., retention time: 21.15 min). After the reaction solution was adjusted to pH 8 with conc. hydrochloric acid, the solution was heated to 70° C., and a solution of potassium cyanate (2.07 g) in distilled water (10 mL) was added dropwise to the solution over 20 minutes. After the completion of the addition, the resultant mixture was stirred for 5 hours, and the reaction solution was sampled for HPLC analysis. As a result, an unreacted amino acid was recognized, and thus a solution of potassium cyanate (4.14 g) in distilled water (20 mL) was further added dropwise to the solution over 20 minutes. After the completion of the addition, the resultant mixture was further stirred for 1 hour, allowed to cool down to room temperature, and then adjusted to pH 2 with conc. hydrochloric acid. The precipitated solid was filtered off, washed with water, and then dried. The $^1$H NMR analysis of the solid showed the production of the target compound (3.38 g, yield 66%).

Example 1

Method for producing N-carbamoyl-S-tert-butyl-α-methyl-L-cysteine and D-5-tert-butylthiomethyl-5-methylhydantoin According to the culture method and the method for preparing an immobilized enzyme described in WO96/20275, the *Bacillus* sp. KNK245 strain (FERM BP-4863) was cultured, and then cells were collected and disrupted by ultrasonic waves to produce an enzyme solution. Then, an anion exchange resin, Duolite A-568, was added as an immobilization support to the enzyme solution to adsorb the resulting enzyme thereon. Furthermore, cross-linking was performed by glutaraldehyde to obtain immobilized hydantoinase.

Next, 1.5 ml of a 0.1 M potassium phosphate buffer (pH 7.0) and 0.003 ml of a 0.5 M aqueous manganese sulfate solution were added to 15 mg of the racemic N-carbamoyl-S-tert-butyl-α-methylcysteine produced in REFERENCE EXAMPLE 2, and the resultant solution was adjusted to pH 6.5 with a 10 N aqueous sodium hydroxide solution. Then, 200 mg (wet weight) of the immobilized hydantoinase prepared as described above was added to the solution, and reaction was performed by stirring at 40° C. for 48 hours. During the reaction, the pH was kept at about 6.5 using 6 N hydrochloric acid. As a result of the HPLC analysis (column: COSMOSIL 5C8-MS, mobile phase: acetonitrile/10 mM aqueous potassium dihydrogen phosphate solution=3/7, flow rate: 0.8 ml/min, detection wavelength: 210 nm, column temperature: 40° C.) of the reaction solution, the residual ratio of the N-carbamoyl-S-tert-butyl-α-methylcysteine was 41%. Also, as a result of the HPLC analysis (column: CHIRALPAK AS (produced by Daicel Chemical Industries, Ltd.), mobile phase: hexane/isopropanol/trichloroacetic acid=7/3/0.01, flow rate: 0.5 ml/min, detection wavelength: 210 nm, column temperature: 30° C.) of the N-carbamoyl-S-tert-butyl-α-methylcysteine contained in the reaction solution, the optical purity was 96.7% ee. Furthermore, the resulting optically active N-carbamoyl-S-tert-butyl-α-methylcysteine was converted to methylcysteine by the method described in EXAMPLES 9 and 10, and the optical rotation of the compound was measured. As a result, it was confirmed that the optically active N-carbamoyl-S-tert-butyl-α-methylcysteine was the L-isomer.

On the other hand, the precipitated compound produced by the enzymatic reaction was extracted with ethyl acetate, and analyzed by chiral HPLC (column: CHIRALPAK AD (produced by Daicel Chemical Industries, Ltd.), mobile phase: hexane/isopropanol=10/3, flow rate: 1 ml/min, detection wavelength: 210 nm, column temperature: 30° C.). As a result, the elution time coincided with that of a standard sample, and it was thus confirmed that the compound was optically active 5-tert-butylthiomethyl-5-methylhydantoin (a chemical purity of 88% and an optical purity of 100% ee, which were determined by the area ratio). Also, as a result of HPLC analysis (column: CHIRALPAK AD (produced by Daicel Chemical Industries, Ltd.), mobile phase: hexane/isopropanol=10/1, flow rate: 1 ml/min, detection wavelength: 210 nm, column temperature: 30° C., D-isomer: 14.7 min, L-isomer: 25.3 min), it was confirmed by comparison with the retention time of a separately synthesized standard sample that the optically active 5-tert-butylthiomethyl-5-methylhydantoin was the D-isomer.

N-carbamoyl-S-tert-butyl-α-methyl-L-cysteine: $^1$H NMR (300 MHz, $CD_3OD$) δ: 3.22 (d, 1H), 3.16 (d, 1H), 1.52 (s, 3H), 1.29 (s, 9H)

D-5-tert-butylthiomethyl-5-methylhydantoin: $^{1}$H NMR (300 MHz, CDCl$_3$ with 3 drops of CD$_3$OD) δ: 2.90 (d, 1H), 2.80 (d, 1H), 1.49 (s, 3H), 1.30 (s, 9H)

Example 2

Method for producing
N-carbamoyl-S-tert-butyl-α-methyl-L-cysteine using
transformed microorganisms of *Escherichia coli*
HB101 pTH104

Transformed microorganisms of *Escherichia coli* HB101 pTH104 (FERM BP-4864) containing a hydantoinase gene derived from the *Bacillus* sp. KNK245 strain (FERM BP-4863) were inoculated into 10 ml of a liquid medium (containing 10 g/l tryptone, 10 g/l yeast extract, and 5 g/l NaCl with pH 7 and prepared by sterilizing at 120° C. for 15 minutes and then adding 100 mg/l of ampicillin through filer sterilization), followed by shaking culture at 37° C. for 18 hours. In a 500-ml of Sakaguchi flask, 1 ml of the culture solution was then inoculated into 50 ml of a liquid medium (10 g/l tryptone, 10 g/l yeast extract, 5 g/l NaCl, pH 7) which was sterilized at 120° C. for 15 minutes, followed by shaking culture at 37° C. for 24 hours. Then, the cells collected from 1 ml of the culture solution by centrifugation were suspended in 1.5 ml of a 0.1 M potassium phosphate buffer (pH 7.0), and 150 mg of racemic N-carbamoyl-S-tert-butyl-α-methylcysteine and 0.003 ml of a 0.5 M aqueous solution of manganese sulfate were added to the resulting suspension. Then, the resulting mixture was adjusted to pH 6.5 with a 10 N aqueous solution of sodium hydroxide, and subjected to reaction by stirring at 40° C. for 24 hours while maintaining the pH at about 6.5 using 6 N hydrochloric acid. As a result of the HPLC analysis (column: COSMOSIL 5C8-MS, mobile phase: acetonitrile/10 mM aqueous potassium dihydrogen phosphate solution ~3/7, flow rate: 0.8 ml/min, detection wavelength: 210 nm, column temperature: 40° C.) of the reaction solution, the residual ratio of N-carbamoyl-5-tert-butyl-α-methylcysteine was 49%. Also, as a result of the HPLC analysis (column: CHIRALPAK AS (produced by Daicel Chemical Industries, Ltd.), mobile phase: hexane/isopropanol/trichloroacetic acid=7/3/0.01, flow rate: 0.5 ml/min, detection wavelength: 210 nm, column temperature: 30° C.) of N-carbamoyl-S-tert-butyl-α-methylcysteine contained in the reaction solution, the optical purity was 94.6% ee. It was also confirmed by comparison with the retention time of the N-carbamoyl-S-tert-butyl-α-methyl-L-cysteine produced in EXAMPLE 1 that the resultant N-carbamoyl-S-tert-butyl-α-methylcysteine was the L-isomer.

Example 3

Method for producing
N-carbamoyl-S-tert-butyl-α-methyl-L-cysteine using
bacteria of the genus *Bacillus*

In a 500-ml Sakaguchi flask, dry preserved cells of the *Bacillus* sp. KNK245 strain (FERM BP-4863) were inoculated into 100 ml of a liquid medium (10 g/l polypeptone, 10 g/l meat extract, 5 g/l yeast extract, pH 7.5) which was sterilized at 120° C. for 15 minutes, followed by shaking culture at 45° C. for 15 hours. Furthermore, 2 ml of the culture solution was inoculated into an above described medium containing the additional components, 1 g/l uracil, and 20 mg/l manganese chloride, followed by shaking culture at 45° C. for 24 hours. Then, the cells collected from 15 ml of the culture solution by centrifugation were suspended in 1.5 ml of a 0.1 M potassium phosphate buffer (pH 7.0), and 150 mg of racemic N-carbamoyl-S-tert-butyl-α-methylcysteine and 0.003 ml of a 0.5 M aqueous solution of manganese sulfate were added to the resulting suspension. Then, the resulting mixture was adjusted to pH 6.5 with a 10 N aqueous solution of sodium hydroxide, and subjected to reaction by stirring at 40° C. for 19 hours while maintaining the pH at about 6.5 using 6 N hydrochloric acid. As a result of the HPLC analysis (column: COSMOSIL 5C8-MS, mobile phase: acetonitrile/10 mM aqueous potassium dihydrogen phosphate solution=3/7, flow rate: 0.8 ml/min, detection wavelength: 210 nm, column temperature: 40° C.) of the reaction solution, the residual ratio of N-carbamoyl-S-tert-butyl-α-methylcysteine was 44%. Also, as a result of the HPLC analysis (column: CHIRALPAK AS (produced by Daicel Chemical Industries, Ltd.), mobile phase: hexane/isopropanol/trichloroacetic acid=9/1/0.01, flow rate: 0.5 ml/min, detection wavelength: 210 nm, column temperature: 30° C.) of N-carbamoyl-S-tert-butyl-α-methylcysteine contained in the reaction solution, the optical purity was 99.0% ee. It was also confirmed by comparison with the retention time of the N-carbamoyl-S-tert-butyl-α-methyl-L-cysteine produced in EXAMPLE 1 that the resultant N-carbamoyl-S-tert-butyl-α-methylcysteine was the L-isomer.

Example 4

Method for producing
N-carbamoyl-S-tert-butyl-α-methyl-L-cysteine using
bacteria of the genus *Pseudomonas*

*Pseudomonas putida* IFO12996 was cultured in a solid medium (containing 10 g/l polypeptone, 2 g/l yeast extract, 1 g/l magnesium sulfate heptahydrate, and 15 g/l agar with pH 7.0) at 30° C. for 24 hours. In a 500-ml Sakaguchi flask, one platinum loop of the cultured cells was inoculated into 100 ml of a liquid medium (20 g/l meat extract, 6 g/l glycerol, 1 g/l uracil, 2 g/l potassium dihydrogen phosphate, 1 g/l magnesium sulfate heptahydrate, 40 mg/l calcium chloride dihydrate, 20 mg/i ferrous sulfate heptahydrate, 20 mg/l manganese sulfate tetrahydrate to hexahydrate, 20 mg/l copper sulfate pentahydrate, pH 5.5) which was sterilized at 120° C. for 15 minutes, followed by shaking culture at 30° C. for 24 hours. Then, the cells collected from 10 ml of the culture solution by centrifugation were suspended in 1 ml of a 0.1 M potassium phosphate buffer (pH 7.0), and 10 mg of racemic N-carbamoyl-S-tert-butyl-α-methylcysteine and 0.002 ml of a 0.5 M aqueous solution of manganese sulfate were added to the resulting suspension. Then, the resulting mixture was subjected to reaction by stirring at 40° C. for 50 hours while maintaining the pH at about 6.5 using 6 N hydrochloric acid. As a result of the HPLC analysis (column: COSMOSIL 5C8-MS, mobile phase: acetonitrile/10 mM aqueous potassium dihydrogen phosphate solution=3/7, flow rate: 0.8 ml/min, detection wavelength: 210 nm, column temperature: 40° C.) of the reaction solution, the residual ratio of N-carbamoyl-S-tert-butyl-α-methylcysteine was 52%. Also, as a result of the HPLC analysis (column: CHIRALPAK AS (produced by Daicel Chemical Industries, Ltd.), mobile phase: hexane/isopropanol/trichloroacetic acid=9/1/0.01, flow rate: 0.5 ml/min, detection wavelength: 210 nm, column temperature: 30° C.) of N-carbamoyl-S-tert-butyl-α-methylcysteine contained in the reaction solution, the optical purity was 95.6% ee. It was also confirmed by composition with the retention time of the N-carbamoyl-S-tert-butyl-α-methyl-L-cysteine produced in EXAMPLE 1 that the resultant N-carbamoyl-S-tert-butyl-α-methylcysteine was the L-isomer.

Example 5

Method for producing N-carbamoyl-S-tert-butyl-α-methyl-L-cysteine using bacteria of the genus *Agrobacterium*

In a large test tube, the *Agrobacterium* sp. KNK712 strain (FERM BP-1900) was inoculated into 10 ml of a liquid medium (containing 10 g/l polypeptone, 10 g/l meat extract, 5 g/l yeast extract, 5 g/l glycerin, 5 g/l potassium dihydrogen phosphate, and 5 g/l disodium hydrogen phosphate with pH 6.5) which was sterilized 120° C. for 15 minutes, followed by shaking culture at 30° C. for 24 hours. Then, 1 ml of the culture solution was inoculated into 100 ml of a liquid medium (containing 25 g/l glycerin, 5 g/l sucrose, 5 g/l potassium dihydrogen phosphate, 5 g/l disodium hydrogen phosphate, 1 g/l magnesium phosphate heptahydrate, 10 mg/l manganese chloride tetrahydrate, and 4 g/l yeast extract with pH 6.5, and prepared by sterilization at 120° C. for 15 minutes and then adding 2 g/l urea and 1 g/l D-N-carbamoyl-α-p-hydroxyphenylglycine through filter sterilization), followed by shaking culture at 33° C. for 23 hours. Then, the cells collected from 5 ml of the culture solution by centrifugation were suspended in 1 ml of a 0.1 M potassium phosphate buffer (pH 7.0), and 10 mg of racemic N-carbamoyl-S-tert-butyl-α-methylcysteine and 0.002 ml of a 0.5 M aqueous solution of manganese sulfate were added to the resulting suspension. Then, the resulting mixture was subjected to reaction by stirring at 40° C. for 5 hours while maintaining the pH at about 6.5 using 6 N hydrochloric acid. As a result of the HPLC analysis (column: COSMOSIL 5C8-MS, mobile phase: acetonitrile/10 mM aqueous potassium dihydrogen phosphate solution=3/7, flow rate: 0.8 ml/min, detection wavelength: 210 nm, column temperature: 40° C.) of the reaction solution, the residual ratio of N-carbamoyl-S-tert-butyl-α-methylcysteine was 23%. Also, as a result of the HPLC analysis (column: CHIRALPAK AS (produced by Daicel Chemical Industries, Ltd.), mobile phase: hexane/isopropanol/trichloroacetic acid=9/1/0.01, flow rate: 0.5 ml/min, detection wavelength: 210 nm, column temperature: 30° C.) of N-carbamoyl-S-tert-butyl-α-methylcysteine contained in the reaction solution, the optical purity was 85.8% ee. It was also confirmed by comparison with the retention time of the N-carbamoyl-S-tert-butyl-α-methyl-L-cysteine produced in EXAMPLE 1 that the resultant N-carbamoyl-S-tert-butyl-α-methylcysteine was the L-isomer.

Example 6

Method for producing D-5-tert-butylthiomethyl-5-methylhydantoin

In order to remove S-tert-butyl-α-methyl-L-cysteine contained as an impurity in the mixture (50 g) of the enzyme and D-5-tert-butylthiomethyl-5-methylhydantoin obtained by the method in EXAMPLE 3, water (400 g) was added to the mixture, followed by stirring. Then, the insoluble substance was filtered off and washed with water (200 g), and a 5 wt % aqueous sodium hydroxide solution (120 g) was added to the filtrate, followed by stirring. Then, the enzyme was filtered off as an insoluble substance, and the filtrate was adjusted to pH 9 with conc. hydrochloric acid. The precipitated crystals were filtered off, washed with water, and then dried under reduced pressure to obtain a crude product as crystals (19.7 g). As a result of the HPLC analysis (column: COSMOSIL 5C8-MS, mobile phase: acetonitrile/potassium dihydrogen phosphate-phosphoric acid solution (pH 2.0)=2/8, flow rate: 1.0 ml/min, detection wavelength: 210 nm, column temperature: 40° C.) of the crude product, the purity and yield calculated by comparison with a standard sample were 87.5 wt % and 79.6%, respectively. Also, as a result of HPLC analysis (column: CHIRALPAK AS (produced by Daicel Chemical Industries, Ltd.), mobile phase: hexane/isopropanol=9/1, flow rate: 1.0 ml/min, detection wavelength: 210 nm, column temperature: 30° C., retention time: D-isomer=15.2 min, L-isomer=39.8 min), the optical purity was 97.6% ee.

Example 7

Method for producing S-tert-butyl-α-methyl-D-cysteine

The mixture (80 g) of D-5-tert-butylthiomethyl-5-methylhydantoin and the enzyme produced by the method in any one of EXAMPLES 1 to 5 was dissolved in a 10 wt % aqueous lithium hydroxide solution (150 mL). The enzyme was removed by filtration, and then D-5-tert-butylthiomethyl-5-methylhydantoin contained in the mother liquid was quantitatively analyzed by HPLC (under the same analytical conditions as in EXAMPLE 6). As a result, the amount of the compound contained in the mother liquid was 44.2 g. Then, lithium hydroxide (54 g) and distilled water (51 g) were added to the solution, and the resultant mixture was refluxed under heating for 38 hours. The mixture was allowed to cool down to room temperature, and the produced solid was filtered off. Then, conc. hydrochloric acid (110 g) was added to the mother liquid kept at an internal temperature of about 20° C. to control the pH to 6.7. Then, the solution was cooled to an internal temperature of 2° C. and stirred for 2 hours. Next, the produced solid was filtered off and dried in vacuum at 40° C. for 24 hours to obtain dry crystals (34.9 g). As a result of HPLC analysis (column: COSMOSIL 5C18-AR (produced by Nacalai Tesque Inc.), mobile phase: potassium dihydrogen phosphate-phosphoric acid solution (pH 2.0)/acetonitrile=90/10, flow rate: 1.0 ml/min, detection wavelength: 210 nm, column temperature: 40° C.), it was confirmed that the solid was the desired compound. The purity and yield were determined by comparison with the authentic sample (purity 96.7 wt %, yield 85.7%).

Example 8

Method for producing α-methyl-D-cysteine hydrochloride

S-tert-butyl-α-methyl-D-cysteine (20 g) was dissolved in conc. hydrochloric acid (180 g), and the resultant solution was refluxed under heating for 45 hours. The reaction solution was allowed to cool down to room temperature, and then concentrated to 35 g. Then, the solution was heated to 40° C., and toluene (110 mL) was added to the solution, followed by concentration to about 40 g. This operation was further repeated four times, and the produced solid was filtered off and dried under vacuum at 60° C. for 48 hours to obtain the title compound as a white solid (15.3 g). As a result of HPLC analysis (column: CAPCELL PAK SCX (produced by Shiseido Co., Ltd.), mobile phase: potassium dihydrogen phosphate-phosphoric acid solution (pH 2.0)/acetonitrile=95/5, flow rate: 0.3 ml/min, detection wavelength: 210 nm, column temperature: 30° C.), it was confirmed that the solid was the desired compound (yield 84.6%). The measurement of optical rotation showed $[\alpha]^D{}_{20}=-6.28$ (c1. 21, H$_2$O). Since the sign of the optical rotation was opposite to that of the α-methyl-L-cysteine hydrochloride produced in EXAMPLE 10, it was confirmed that the obtained compound was the intended D-stereoisomer.

Example 9

Method for producing α-methyl-L-cysteine hydrochloride

N-carbamoyl-S-tert-butyl-α-methyl-L-cysteine (100 mg, 0.43 mmol) was dissolved in conc. hydrochloric acid (1 mL), and the resultant solution was refluxed in nitrogen for 60 hours to prepare an aqueous solution of α-methyl-L-cysteine hydrochloride.

Example 10

Method for producing α-methyl-L-cysteine hydrochloride

Isopropyl alcohol (0.5 mL) was added to the reaction solution of α-methyl-L-cysteine hydrochloride obtained in EXAMPLE 9, and the resultant mixture was concentrated under reduced pressure and dried by azeotropic dehydration. This operation was repeated three times until the volume became about ⅓ by concentration. Then, the residue was heated to 60° C., and toluene (1 mL) was added to the residue. After the mixture was allowed to cool down to room temperature under stirring, stirring was continued for about 1 hour. Then, the precipitated crystals were filtered off, washed with toluene, and dried under reduced pressure to obtain the title compound as a white solid (44.3 mg). As a result of HPLC analysis (under the same analytical conditions as in EXAMPLE 8), it was confirmed that the solid was the desired compound (yield 60.0%). The measurement of optical rotation showed $[\alpha]^D{}_{20}=8.77$ (c1. 15, H$_2$O). Since the sign of the optical rotation coincided with the value in the reference (Tetrahedron, 1993, 49, 2131-2138, WO98/38177), it was confirmed that the obtained compound was the intended L-stereoisomer.

$^1$H NMR (300 MHz, D$_2$O) δ: 3.18 (d, 1H), 2.89 (d, 1H), 1.60 (s, 3H)

Example 11

Method for producing S-tert-butyl-α-methyl-L-cysteine

N-carbamoyl-S-tert-butyl-α-methyl-L-cysteine (82.4 g, 351.4 mmol) was dissolved in a 18% aqueous lithium hydroxide solution (630 g), and the resultant solution was refluxed in nitrogen for 41 hours. After the solution was allowed to cool down to room temperature, the insoluble substance was filtered off, and the filtrate was adjusted to pH 6 by adding conc. hydrochloric acid (180.1 g). After stirring for about 1 hour, the mixture was cooled to 4° C. to 5° C., and further stirred for 1 hour. The produced crystals were filtered off, washed with water, and then dried under reduced pressure to obtain the title compound as a white solid (53.9 g). As a result of HPLC analysis (column: COSMOSIL 5C18-AR (produced by Nacalai Tesque Inc.), mobile phase: potassium dihydrogen phosphate-phosphoric acid solution (pH 2.0)/acetonitrile=90/10, flow rate: 1.0 ml/min, detection wavelength: 210 nm, column temperature: 40° C.), it was confirmed that the solid was the desired compound (yield 85.7%)

$^1$H NMR (300 MHz, D$_2$O) δ: 3.18 (d, 1H), 2.91 (d, 1H), 1.60 (s, 3H), 1.35 (s, 9H)

Example 12

Method for producing α-methyl-L-cysteine hydrochloride

Conc. hydrochloric acid (345.3 g) was added to S-tert-butyl-α-methyl-L-cysteine (38.4 g, 201 mmol) produced by the method in EXAMPLE 11, and the resultant mixture was refluxed for 24 hours to obtain an aqueous solution of α-methyl-L-cysteine hydrochloride.

Example 13

Method for isolating α-methyl-L-cysteine hydrochloride

The reaction solution of α-methyl-L-cysteine hydrochloride obtained in EXAMPLE 12 was concentrated to 67.5 g (degree of vacuum: 30 to 60 mmHg, temperature: 45° C.), and toluene (206 g) was added to the residue. Again a vacuum concentration operation (degree of vacuum: 40 to 60 mmHg, temperature: 40° C., distillation rate: 107 L/h·m$^2$) was performed until the total was 109 g, and toluene (206 g) was further added to the residue, followed by concentration. The same operation was repeated six times in total to obtain a toluene slurry (104 g) of the product, α-methyl-L-cysteine hydrochloride. The water content of the slurry was 30% by weight (based on α-methyl-L-cysteine hydrochloride). The slurry was filtered, and the obtained crystals were washed with toluene and dried under reduced pressure (at 0 to 100 mmHg and 30° C. to 80° C. for 5 to 10 hours) to obtain the title compound as a white solid (32.2 g, yield 93.4%).

Example 14

Method for producing α-methyl-L-cysteine hydrochloride

First, water (47.6 g) and conc. hydrochloric acid (177.4 g) were added to S-tert-butyl-α-methyl-L-cysteine (25 g, 131 mmol) produced by the method of EXAMPLE 11, and the resultant mixture was refluxed for 41 hours. Furthermore, conc. hydrochloric acid (47.6 g) was added to the mixture, followed by reflux for 3 hours. After the mixture was allowed to cool down to room temperature, isopropyl alcohol (90 mL) was added to the mixture, followed by vacuum concentration. Then, azeotropic dehydration was performed three times using the same amount of isopropyl alcohol. Finally, isopropyl alcohol was added to the residue, and the resultant mixture was concentrated to a volume of about ⅓. Then, the residue was heated to 60° C., and toluene (90 mL) was added to the residue. After the mixture was allowed to cool down to room temperature under stirring, stirring was continued about 1 hour. Then, the precipitated crystals were filtered off, washed with toluene, and dried under reduced pressure to obtain the title compound as a white solid (13.5 g, yield 60.0%).

Example 15

Method for producing D-5-mercaptomethyl-5-methylhydantoin

First, D-5-tert-butylthiomethyl-5-methylhydantoin (4.38 g) produced in EXAMPLE 6 was dissolved in conc. hydrochloric acid (100 g), and the resultant solution was stirred at 80° C. for 18.5 hours. After the solution was allowed to cool down to room temperature, the solution was concentrated to about a half, and the residue was adjusted to pH 0 by adding 30.5 g of a 30 wt % aqueous sodium hydroxide solution. After extraction with ethyl acetate (100 mL×3), the organic phase was concentrated to 10% of the total, and toluene (30 mL) was added to the residue. The precipitated crystals were filtered off to obtain the target D-5-mercaptomethyl-5-methylhydantoin (2.65 g) in a yield of 80%. As a result of the measure of the optical purity of this compound by HPLC (CHIRALPAK AS (produced by Daicel Chemical Industries, Ltd.), mobile phase: hexane/isopropanol=9/1, flow rate: 1.0 ml/min, detection wavelength: 210 nm, column temperature: 35° C., retention time: D-isomer; 30.4 min, L-isomer; 33.8 min), the L-isomer was not detected.

$^1$H NMR (400 MHz, MeOH-d4) δ: 1.32 (s, 3H), 2.60 (d, 1.6 Hz, 1H), 2.72 (d, 1.6 Hz, 1H)

Example 16

Method for Determining Optical Purity of α-Methyl-L-Cysteine Hydrochloride

First, α-methyl-L-cysteine hydrochloride (74.9 mg, 0.44 mmol) produced by the method of EXAMPLE 13 was dissolved in water (3 mL), and sodium hydrogen carbonate (197.7 mg) and ethanol (3 mL) were added to the resultant solution. After nitrogen purge, benzyl chlorocarbonate (0.17 mL, 1.10 mmol) was added to the resultant mixture, followed by stirring at room temperature for 2 days. Then, conc. hydrochloric acid was added to the reaction solution to adjust the solution to pH 1.9, and extraction was performed with ethyl acetate. Then, the organic phase was dried over anhydrous sodium sulfate, and the solvent was distilled off under reduced pressure. As a result of the PTLC (hexane/ethyl acetate=1/1 with a small amount of acetic acid) purification and $^1$H NMR analysis of the residue, it was confirmed that the desired compound (106 mg, yield 60%) was produced. The HPLC analysis (column: CHIRALCEL OD-RH (produced by Daicel Chemical Industries, Ltd.), mobile phase: potassium dihydrogen phosphate-phosphoric acid solution (pH 2.0)/acetonitrile=6/4, flow rate: 1.0 ml/min, detection wavelength: 210 nm, column temperature: 30° C., retention time: 19.15 min (D), 22.92 min (L)) of the compound showed an optical purity of 98.6% ee.

$^1$H NMR (300 MHz, D$_2$O) δ: 7.30-7.40 (m, 10H), 5.22 (s, 2H), 5.10 (s, 2H), 3.60 (s, 2H), 1.63 (s, 3H)

Examples 17 to 21

Method for producing N-carbamoyl-S-tert-butyl-α-methyl-cysteine

First, sodium hydroxide and water were added to 5-tert-butylthiomethyl-5-methylhydantoin, and the resultant mixture was heated to a predetermined temperature and stirred. The reaction solution was analyzed by HPLC (column: COSMOSIL 5C18-AR (produced by Nacalai Tesque Inc.), mobile phase: acetonitrile/10 mM aqueous potassium dihydrogen phosphate solution=30/70, flow rate: 1.0 ml/min, detection wavelength: 210 nm, column temperature: 40° C.) to determine the yield of the title compound. The results are shown in Table 1.

TABLE 1

| Example | NaOH (molar equivalent) | Water (times by weight) | Reaction temperature (° C.) | Reaction time (hour) | Yield (%) |
|---|---|---|---|---|---|
| 17 | 3.3 | 1.4 | 90 | 44 | 82 |
| 18 | 3.3 | 1.4 | 95 | 15 | 81 |
| 19 | 3.3 | 1.4 | 100 | 9 | 64 |
| 20 | 2.2 | 1.0 | 95 | 13 | 80 |
| 21 | 1.6 | 0.7 | 95 | 6 | 54 |

Example 22

Method for producing N-carbamoyl-S-tert-butyl-α-methyl-cysteine

First, 5-tert-butylthiomethyl-5-methylhydantoin (5 g, 23 mmol) was mixed with a 58% aqueous potassium hydroxide solution (9.2 g), and the mixture was heated to 95° C. and stirred for 22 hours. The HPLC analysis of the reaction solution showed the production of the title compound in a reaction yield of 92%.

Example 23

Method for producing N-carbamoyl-S-tert-butyl-α-methyl-cysteine

First, 5-tert-butylthiomethyl-5-methylhydantoin (5 g, 23 mmol) was mixed with a 65% aqueous potassium hydroxide solution (4.4 g) and toluene (5 ml), and the mixture was heated to 95° C. and stirred for 27 hours. The HPLC analysis of the reaction solution showed the production of the title compound in a reaction yield of 88%.

Example 24

Method for producing N-carbamoyl-S-tert-butyl-α-methyl-cysteine

First, 5-tert-butylthiomethyl-5-methylhydantoin (5 g, 23 mmol) was mixed with a 73% aqueous potassium hydroxide solution (5.7 g) and toluene (10 ml), and the mixture was heated to 95° C. and stirred for 51 hours. The HPLC analysis of the reaction solution showed the production of the title compound in a reaction yield of 90%.

Example 25

Method for producing N-carbamoyl-2-amino-2-methyl propionic acid

First, 4.0 g of 5,5-dimethylhydantoin was mixed with 4.0 g of sodium hydroxide and 4.0 g of water, and the mixture was stirred at 85° C. to 90° C. for 3.5 hours. The HPLC analysis (column: COSMOSIL 5C18-ARII (produced by Nacalai Tesque Inc.), mobile phase: acetonitrile/10 mM aqueous potassium dihydrogen phosphate solution=20/80, flow rate: 0.5 ml/min, detection wavelength: 210 nm, column temperature: 40° C.) of the reaction mixture showed the production of 3.38 g (yield 74.1%) of the title compound.

$^1$H NMR (300 MHz, D$_2$O) δ: 1.39 (s, 6H)

Example 26

Method for producing N-carbamoyl-2-amino-3-(2-methoxyphenyl)-2-methyl propionic acid First, 4.40 g of 5-(2-methoxyphenylmethyl)-5-methyl-hydantoin was mixed with 2.64 g of sodium hydroxide and 3.5 g of water, and the mixture was subjected to reaction at 94° C. to 96° C. for 30 hours. The HPLC analysis (column: COSMOSIL 5C18-ARII (produced by Nacalai Tesque Inc.), mobile phase: acetonitrile/10 mM aqueous potassium dihydrogen phosphate solution=20/80, flow rate: 1.0 ml/min, detection wavelength: 210 nm, column temperature: 40° C.) of the reaction mixture showed the production of the title compound, 2-amino-3-(2-methoxyphenyl)-2-methyl propionic acid, and the raw material at an area ratio of 78.8:5.5:15.5.

$^1$H NMR (300 MHz, D$_2$O) δ: 7.32-6.90 (m, 4H), 4.84 (s, 3H), 3.19 (d, 1H), 3.18 (d, 1H), 1.37 (s, 3H)

Example 27

Method for producing N-carbamoyl-S-benzyl-α-methylcysteine

First, 5.0 g of 5-benzylthiomethyl-5-methylhydantoin was mixed with 3.6 g of potassium hydroxide and 3 g of water, and the mixture was subjected to reaction at 94° C. to 96° C. for 12 hours. The HPLC analysis (column: COSMOSIL 5C18-ARII (produced by Nacalai Tesque Inc.), mobile phase: acetonitrile/10 mM aqueous potassium dihydrogen phosphate solution=30/70, flow rate: 1.0 ml/min, detection wavelength: 254 nm, column temperature: 40° C.) of the reaction mixture showed the production of 3.56 g yield 66.4%) of the title compound.

$^1$H NMR (300 MHz, D$_2$O) δ: 7.40-7.30 (m, 5H), 3.78 (s, 2H), 3.15 (d, 1H), 3.14 (d, 1H), 1.41 (s, 3H)

Comparative Example 1

Method for producing N-carbamoyl-S-tert-butyl-α-methylcysteine

First, 5-tert-butylthiomethyl-5-methylhydantoin (5 g, 23 mmol) was mixed with barium hydroxide (11.7), and water (10 g), and the mixture was heated to 95° C. and stirred for 2 hours. The HPLC analysis of the reaction solution showed the production of the title compound in a reaction yield of 39%.

Comparative Example 2

Method for producing N-carbamoyl-S-tert-butyl-α-methyl-cysteine (according to the method described in U.S. Pat. No. 5,338,859)

First, 5-tert-butylthiomethyl-5-methylhydantoin (purity content 10.82 g, 50.0 mmol) was mixed with calcium hydroxide (3.70 g, 50.0 mmol), and water (60 g), and the mixture was heated to 100° C. and stirred for 3.5 hours. The HPLC analysis of the reaction solution showed the production of the title compound in a reaction yield of 25%.

INDUSTRIAL APPLICABILITY

As described above, according to the present invention, both the D- and L-isomers of an optically active α-methyl-cysteine derivative or its salt, which is useful as an pharmaceutical intermediate, can be produced from readily available, inexpensive raw materials by a simple, industrially practical process. Also, the compound can be obtained as crystals by an industrially practical means.

The invention claimed is:

1. A process for, producing α-methyl-D-cysteine represented by formula (9) or its salt:

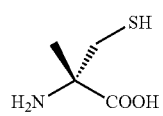

(9)

the process comprising
hydrolyzing a D-5-methyl-5-thiomethylhydantoin derivative represented by formula (2) or its salt:

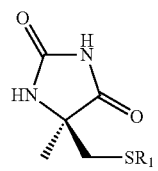

(2)

(wherein R$^1$ represents a substituted or unsubstituted alkyl group having 1 to 20 carbon atoms, a substituted or unsubstituted aralkyl group having 7 to 20 carbon atoms, or a substituted or unsubstituted aryl group having 6 to 20 carbon atoms) to produce an α-methyl-D-cysteine derivative represented by formula (8) or its salt:

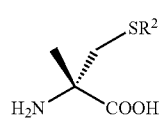

(8)

(wherein R$^2$ is the same as R$^1$), and
treating the α-methyl-D-cysteine derivative represented by formula (8) or its salt with an acid to deprotect the sulfur atom.

2. The process according to claim 1, wherein hydrolysis is performed with an alkali to produce a compound represented by formula (8) in which R$^2$ is the same as R$^1$ in formula (2).

3. The process according to claim 2, wherein the alkali used in the hydrolysis is sodium hydroxide, potassium hydroxide, lithium hydroxide, barium hydroxide, magnesium hydroxide, or calcium hydroxide.

4. The process according to claim 1, comprising adding an acid to the reaction solution after hydrolysis reaction to decrease the pH and crystallize a compound represented by formula (8), thereby obtaining the compound as crystals.

5. The process according to claim 4, wherein the acid used is any one selected from hydrochloric acid, sulfuric acid, hydrobromic acid, nitric acid, acetic acid, and trifluoroacetic acid, or a mixed acid of at least two acids selected therefrom.

6. The process according to claim 5, wherein the acid used is hydrochloric acid.

7. The process according to claim 4, wherein the pH of the reaction solution is decreased to 9.5 or less.

8. The process according to claim 1, wherein the acid used for deprotecting the sulfur atom is any one selected from hydrochloric acid, sulfuric acid, hydrobromic acid, nitric acid, acetic acid, and trifluoroacetic acid, or a mixed acid of at least two acids selected therefrom.

9. The process according to claim 1, wherein the acid used for deprotecting the sulfur atom is hydrochloric acid.

10. The process according to claim 1, wherein the compound represented by formula (2) is produced by a process comprising treating a racemic N-carbamoyl-α-methylcysteine derivative represented by formula (1) or its salt with a hydantoinase to selectively cyclize the D-isomer:

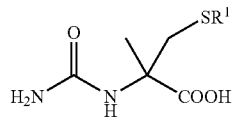 (1)

wherein $R^1$ is the same as $R^1$ in formula (2).

11. The process according to claim 10, wherein the hydantoinase is derived from microorganisms of the genus *Agrobacterium, Bacillus, Pseudomonas* or *Rhizobium*.

12. The process according to claim 10, wherein the hydantoinase is derived from *Agrobacterium* sp. KNK712 (FERM BP-1900), *Bacillus* sp. KNK245 (FERM BP-4863), *Pseudomonas putida* IFO 12996, *Pseudomonas* sp. KNK003A (FERM BP-3181) or *Rhizobium* sp. KNK1415.

* * * * *